US008569237B2

(12) United States Patent
Sheffield

(10) Patent No.: US 8,569,237 B2

(45) Date of Patent: Oct. 29, 2013

(54) CHIMERIC HIRUDIN PROTEINS

(75) Inventor: William P. Sheffield, Hamilton (CA)

(73) Assignee: Canadian Blood Services, Inc., Ottawa, Ontario (CA)

( * ) Notice: Subject to any disclaimer, the term of this patent is extended or adjusted under 35 U.S.C. 154(b) by 325 days.

(21) Appl. No.: 12/619,919

(22) Filed: Nov. 17, 2009

(65) Prior Publication Data

US 2010/0137214 A1 Jun. 3, 2010

Related U.S. Application Data

(60) Provisional application No. 61/115,227, filed on Nov. 17, 2008.

(51) Int. Cl.
*A61K 38/55* (2006.01)
*A61K 38/00* (2006.01)

(52) U.S. Cl.
USPC ......... 514/14.8; 514/14.7; 514/14.9; 530/350

(58) Field of Classification Search
None
See application file for complete search history.

(56) References Cited

U.S. PATENT DOCUMENTS 4,536,391 A * 8/1985 Miyazaki et al. ............ 424/94.3
5,759,542 A * 6/1998 Gurewich .................. 424/94.64

FOREIGN PATENT DOCUMENTS

WO WO 96/04004 A1 2/1996

OTHER PUBLICATIONS

Gosalia et al. (2005) Profiling serine protease substrate specificity with solution phase fluorogenic peptide microarrays, Proteomics, vol. 5, pp. 1292-1298.*

Begbie et. al., An important role for the activation peptide domain in controlling factor IX levels in the blood of haemophilia B mice, Thromb Haemost, Dec. 2005;94(6):1138-47.

Cunningham et al., Altering heparin cofactor II at VAL439 (P6) either impairs inhibition of thrombin or confers elastase resistance. Thromb Haemost, Jul. 2002;88(1):89-97.

Hervio et al., Negative selectivity and the evolution of protease cascades: the specificity of plasmin for peptide and protein substrates, Chem Biol. Jun. 2000:7(6)443-53.

Lazar et al., Hirudin: amino-terminal residues play a major role in the interaction with thrombin. J Biol Chem. Jan. 15, 1991;266(2):685-8.

Mo et al., A novel hirudin derivative characterized with anti-platelet aggregations and thrombin inhibition. J Thromb Thromholysis, Aug. 2009;28(2):230-7. Epub Nov. 9, 2008.

Peter et al., Construction and functional evaluation of a single-chain antibody fusion protein with fibrin targeting and thrombin inhibition after activation by factor Xa. Circulation. Mar. 14, 2000;101(10):1158-64.

Peter et al., Construction and in vitro testing of a novel fab-hirudin-based fusion protein that targets fibrin and inhibits thrombin in a factor xa-dependent manner. J Cardiovasc Pharmacol. Aug. 2003;42(2):237-44.

Sheffield et al., Combined administration of barboarin—albumin and hirudin—albumin fusion proteins limits fibrin(ogen) deposition on the rabbit balloon-injured aorta. Thromb Res. 2007;119(2):195-207. Epub Feb. 14, 2006.

Sheffield et al., Prolonged in vivo anticoagulant activity of a hirudin-albumin fusion protein secreted from *Pichia pastoris*, Blood Coagul Fibrinolysis. Sep. 2001;12(6):433-43.

Sheffield et al., A long-lasting, plasmin-activatable thrombin inhibitor aids clot lysis in vitro and does not promote bleeding in vivo. Thromb Haemost, May 2009;101(5):867-77.

Sheffield et al., Effects of genetic fusion of factor IX to albumin on in vivo clearance in mice and rabbits. Br J Haematol Aug. 2004;126(4):565-73.

Syed et al., Potent antithrombin activity and delayed clearance from the circulation characterize recombinant hirudin genetically fused to albumin. Blood. May 1, 1997;89(9):3243-52.

Zhang et al., Construction and functional evaluation of hirudin derivatives with low bleeding risk. Thromb Haemost. Feb. 2008;99(2):324-30.

GenBank Accession No. CAA02181, PAT Jul. 9, 1996.

GenBank Accession No. P84590, INV Sep. 27, 2005.

GenBank Accession No. CAA51293, INV Nov. 14, 1996.

GenBank Accession No. CAA01205, PAT Mar. 22, 1995.

* cited by examiner

*Primary Examiner* — Manjunath Rao
*Assistant Examiner* — Samuel Liu
(74) *Attorney, Agent, or Firm* — Wolf, Greenfield & Sacks, P.C.

(57) ABSTRACT

The present invention relates to a chimeric hirudin protein comprising a carrier attached to the N-terminus of hirudin, with an intervening plasmin cleavage site. The chimeric hirudin protein contains a relatively inactive form of hirudin. However, when such chimeric hirudin protein being cleaved by plasmin in the vicinity of a clot and, ultimately causing the release of active hirudin and the reduction of the size of the clot. The chimeric hirudin protein exhibited much slower clearance in mice than unfused wild-type hirudin.

11 Claims, 10 Drawing Sheets

CHIMERIC HIRUDIN PROTEINS

CROSS-REFERENCE TO RELATED APPLICATIONS

This application claims priority from U.S. provisional application 61/115, 227 filed on Nov. 17, 2008, herein incorporated in its entirety.

CROSS-REFERENCE TO A SEQUENCE LISTING

This application contains a sequence listing in electronic format which is incorporated in its entirety.

TECHNICAL FIELD

The present invention relates to hirudin and variants thereof, and more specifically to a chimeric protein comprising an activatable but otherwise latent hirudin or analog thereof.

BACKGROUND

The natural regulation of thrombin by its principal native serine proteinase inhibitors (serpins), antithrombin and heparin cofactor II, is thought to become overwhelmed in thrombotic disorders. Although these plasma proteins, in particular in the presence of heparan sulphate or dermatan sulphate glycosaminoglycan cofactors, inhibit thrombin in a suicide substrate mechanism that is likely physiologically irreversible, their affinity for thrombin is much lower than that of the leech protein, hirudin. The hirudins are a family of closely-related small proteins, 65 to 66 amino acids in length, that bind thrombin with sub-picomolar inhibitory constants. As such, they constitute the most potent known polypeptide inhibitors of thrombin.

The potency of hirudin as a thrombin inhibitor originally raised high hopes that it would become a mainstay of interventional cardiology, and other medical areas with unmet clinical needs for antithrombotic and adjunctive anticoagulant agents. Currently, however, recombinant hirudins produced in yeast, such as desirudin and lepirudin, are primarily used in heparin-induced thrombocytopenia, and not in acute coronary syndromes, where extensive investigation failed to show superiority over heparin in primary outcomes. Hemorrhagic complications narrow the therapeutic window of hirudin and limit its applications. Its pharmacokinetics are also a challenge to optimal application. Hirudin's small size and tightly disulphide-bonded, compact structure result in rapid, renally mediated clearance from the circulation. In the laboratory of the present inventor, the clearance of hirudin in animal models has been altered by fusion to albumin (Syed S, Schuyler P D, Kulczycky M, et al., Blood 1997; 89: 3243-3252), and it was demonstrated that lower doses of the fusion protein had anticoagulant and antithrombotic effects greater, or at least more durable, than its smaller predecessor. Nevertheless, the fusion protein still promoted bleeding, and lowering the dose in combination with an antiplatelet protein-albumin fusion only modestly reduced this tendency (Sheffield W P, Gataiance S, Eltringham-Smith L J., Thromb Res 2007; 119: 195-207).

Other efforts to regulate hirudin's potent antithrombin activity have centred on converting it into a prodrug. Extrapolating from the known importance of a free N-terminus for maximal effectiveness of hirudin (Lazar J B, Winant R C, Johnson P H., J Biol Chem 1991; 266: 685-688), a recombinant single chain anti-fibrin antibody fused at its light chain C-terminus to the N-terminus of hirudin, via a factor Xa cleavage site was produced (Peter K, Graeber J, Kipriyanov S, et al., Circulation 2000; 101: 1158-1164). However, the fusion protein had little or no antithrombin activity unless exposed to factor Xa. Similarly, tri- or tetrapeptide factor Xa, factor XIa, or thrombin cleavage sites were added to the N-terminus of hirudin, temporarily blocking its activity, until procoagulant protease cleavage restored its function (Zhang C, Yu A, Yuan B, et al., Thromb Haemost 2008; 99: 324-330).

It would be desirable to have an antithrombotic compound that can be activated to have an antithrombotic activity in the presence of a pathological blood clot which reduces or eliminates blood flow through a blood vessel, and which otherwise would be inactive, thereby reducing the risk of hemorrhagic complications.

SUMMARY

This application concerns novel hirudin chimeric constructs which are activated in the presence of plasmin (in the vicinity of the clot). In their inactive form, these novel chimeric construct have a long half-life in the blood stream and are not eliminated by the kidney.

According to a first aspect, this application provides a chimeric hirudin protein comprising a carrier, a plasmin cleavage site and a hirudin. In an embodiment, the carrier has a molecular weight equal to or greater than 40 kDa and being physiologically acceptable. In another embodiment, the plasmin cleavage site is covalently attached through its amino-terminus to the carrier. The plasmin cleavage site may have the following sequence:

$NH_2$-$X_1$-$X_2$-$X_3$-$X_4$-$X_5$-$X_6$-COOH (SEQ ID NO: 21)

$X_1$, $X_2$ and $X_5$ are the same or different and are an uncharged polar amino acids; $X_3$ is an hydrophobic amino acid or an uncharged polar amino acid; $X_4$ is an hydrophobic amino acid; and $X_6$ is a basic hydrophilic amino acid. In an embodiment, the hirudin is covalently attached by its amino-terminus to the carboxy terminus of the plasmin cleavage site. In these chimeras, the hirudin is releasable from said chimeric hirudin protein in the presence of plasmin. In another embodiment, $X_1$ is a glycine residue. In another embodiment, $X_2$ is a serine residue. In a further embodiment, $X_3$ is an alanine residue or a glycine residue. In yet another embodiment, $X_4$ is a methionine residue or an isoleucine residue. In still a further embodiment, $X_5$ is a serine residue or a tyrosine residue. In yet another embodiment, $X_6$ is an arginine residue or a lysine residue. In still a further embodiment, the sequence of the plasmin cleavage site is SEQ ID NO: 7, SEQ ID NO: 13 or SEQ ID NO: 21. In yet a further embodiment, the carrier is a protein, such as a plasma protein. The plasma protein can be albumin or alpha-1-acid glycoprotein. In still a further embodiment, the hirudin is a hirudin variant 3.

According to a second aspect, the present application also provides an isolated nucleic acid sequence coding for the chimeric hirudin protein described herein. This nucleic acid sequence comprises sequentially a first sequence coding for the carrier operably linked in an open reading frame to a second sequence coding for the plasmin cleavage site, said second sequence being operably linked in the open reading frame to a third sequence coding for the hirudin.

According to a third aspect, the present application provides an expression cassette comprising the isolated nucleic acid sequence described herein. This expression cassette is capable, under appropriate conditions, to express said chimeric hirudin protein.

According to a fourth aspect, the present application also provides a host cell comprising the isolated nucleic acid sequence described herein or the expression cassette described herein. This host cell is capable of expressing, under appropriate conditions, said chimeric hirudin protein.

According to a fifth aspect, the present application also provides a method for limiting the growth of a clot in a subject in need thereof. Broadly, this method comprises the step of administering to the subject the chimeric hirudin protein as defined herein in order to limit the size of said clot. In an embodiment, the chimeric hirudin protein is administered with a thrombolytic agent. In another embodiment, the chimeric hirudin protein is administered after the thrombolytic agent.

According to a sixth aspect, the present application also provides a method for reducing the size of a clot in a subject in need thereof. Broadly, this method comprises the step of administering to the subject the chimeric hirudin protein as defined herein in order to reduce the size of said clot. In an embodiment, the chimeric hirudin protein is administered with a thrombolytic agent. In another embodiment, the chimeric hirudin protein is administered after the thrombolytic agent.

According to a seventh aspect, the present application also provides the use of the chimeric hirudin protein described herein for limiting of the growth of a clot in a subject, for the reduction of the size of a clot in a subject, for the manufacture of a medicament for limiting the growth of a clot in a subject as well as for the manufacture of a medicament for reducing the size of a clot in a subject. In an embodiment, the chimeric hirudin protein is formulated for administration with a thrombolytic agent.

According to an eighth aspect, the present application provides the chimeric hirudin protein described herein for use in limiting the growth of a clot in a subject as well as for use in reducing the size of a clot in a subject. In an embodiment, the chimeric hirudin protein is formulated for administration with a thrombolytic agent.

DETAILED DESCRIPTION

Figure 1A:
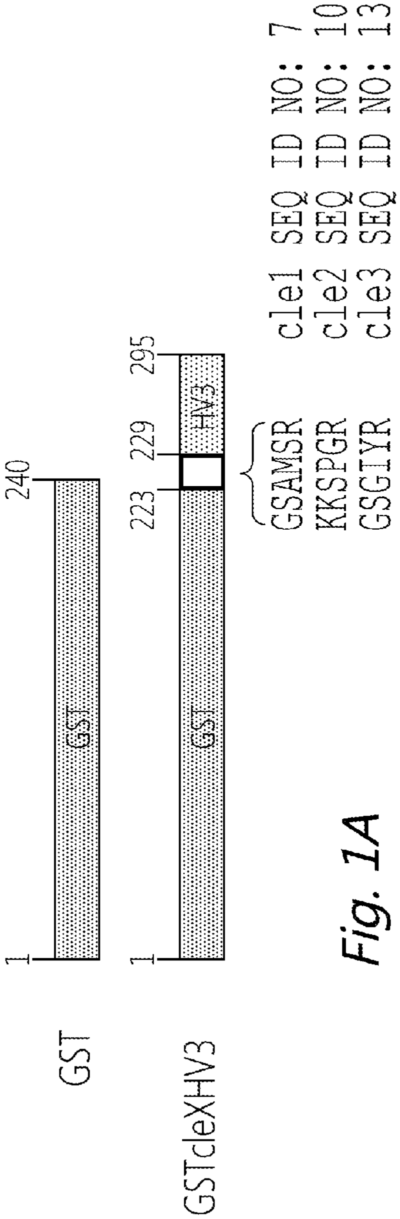
FIG. 1 Glutathione sulfotransferase (GST) fusion proteins. (A) illustrates schematic diagrams ($NH_2$ to COOH) of GST, and three chimeric protein constructs (GSTcleXHV3) comprising GST fused to hirudin variant 3 (HV3) with an intervening plasmin cleavage site (open bar containing cleavage (cle) sequence 1, 2, or 3 corresponding to GSTcle1XHV3 (SEQ ID NO: 7), GSTcle2XHV3 (SEQ ID NO: 10) and GSTcle3XHV3 (SEQ ID NO: 13) respectively), in linear form. (B) illustrates, on the left panel, a Coomassie-Blue stained 10% SDS-acrylamide gel containing (from left to right) purified GSTcle1XHV3, GSTcle2XHV3 and GSTcle3XHV3 proteins, recombinant GST (alone) and HV3RSA (hirudin linked to a rabbit serum albumin and described in Sheffield W P, Gataiance S, Eltringham-Smith L J., Thromb Res 2007; 119: 195-207) (1.0 mg in each case). On the right panel, a replica of the sample-containing lanes of the stained Coomassie-Blue stained gel, transferred to a membrane and probed with a-thrombin. (C) illustrates the release of thrombin-inhibitory activity (% of thrombin inhibition in function of time (minutes)) following incubation of GSTcle1HV3, GSTcle2HV3 and GSTcle3HV3 fusion proteins with plasmin followed by the measurement of the ability of the reaction products to inhibit thrombin. (D) illustrates a Coomassie Blue-stained 16% Tris-Tricine SDS polyacrylamide gel showing the reaction product of 150 nM plasmin (pl) digestion of 15 mM GSTcle3HV3 at 37° C. for 18 hours, compared to purified HV3, GST, and control GSTcle3HV3 that is not incubation with plasmin.

In order to provide a novel antithrombotic agent, it is proposed herein to couple hirudin to (i) a carrier to inhibit hirudin's intrinsic anti-thrombin activity, and to (ii) a plasmin cleavage site so that the hirudin can be released and activated by plasmin in the vicinity of a blood clot. These novel chimeric hirudin proteins possess the advantage of being inactive when they are not located in the vicinity of a clot, thereby limiting the possible side-effects of the presence of high levels of circulating hirudin in the blood stream. In addition, due to the presence of the carrier, they are not easily expelled by the kidneys and as such possess a longer half-life in the blood. Further, because they are likely to be activated in regions where plasmin activity is important, such as in the vicinity of a blood clot, these chimeric hirudin protein are more specific than traditional antithrombotic therapy. These chimeras can both serve as antithrombotic agents as well as adjuncts to usual thrombolytic agents, in coronary interventions and thrombolytic therapy.

According to one aspect, the present application provides a chimeric hirudin protein comprising a carrier, a plasmin cleavage site as well as a hirudin. The amino-terminus of the plasmin cleavage side is covalently coupled to the carrier. This covalent bound can be, for example, an amino peptide bond if the carrier is a polypeptide. Other types of covalent bonding between the carrier and the plasmin cleavage site can also be used. In the chimeric hirudin protein, the amino-terminal end of the hirudin is covalently bound to the carboxy-terminal end of the plasmin cleavage site. This covalent bound between the hirudin and the plasmin cleavage site is preferably an amino peptide bond since both entities are polypeptidic in nature. This amino peptide is scissile by plasmin to release hirudin in settings where plasmin concentration is high enough so that it comes into physical contact with the hirudin chimera. The cleavage of the hirudin chimera can be observed with concentrations of plasmin as low as 100 nM.

The advantages to coupling hirudin to an acceptable carrier such as albumin with a plasmin cleavage site are two-fold:

- Hirudin is inactive when positioned C-terminal to a plasmin cleavage site and a carrier, and acquires the long circulatory half-life of the carrier in vivo.
- Plasmin specifically activates the chimeric protein, liberating active hirudin that inhibits thrombin not only in solution but also bound to fibrin clots.

The chimera inhibits clot extension and enhances clot lysis in a plasmin-dependent manner and, unlike unfused or wild-type hirudin, does not promote bleeding.

The term "carrier", as used herein, refers to a molecule to which it is possible to covalently couple to a plasmin cleavage site. Preferably, the carrier needs not to interfere with the activity of hirudin. Further, it is preferable that the carrier does not cause an immune response (e.g. the carrier is immunologically inert). Still preferably, the carrier has a longer clearance time in the blood stream than hirudin alone. It is known in the art that carriers having a molecular weight equal to or higher than 40 kDa (or even higher than 60 kDa) are less rapidly expelled by the kidney and, consequently, have a longer half-life in blood than molecules or smaller size. The carrier is preferably selected not to participate in the anti-thrombotic/thrombotic process.

In an embodiment, the carrier is a protein or polypeptide, such as, for example, a plasma protein. Plasma proteins include, but are not limited to serum albumin, immunoglobulins (or fragments thereof), alpha-1-acid glycoprotein, transferrin, or lipoproteins. In another embodiment, the carrier is not polypeptidic in nature, but is rather a chemical polymer. Such polymers include, but are not limited to, PEG.

As used herein, the term "plasmin cleavage site" refers to a short stretch of amino acids that is cleaved by plasmin. The cleavage of the chimeric hirudin protein releases active hirudin from the chimera. In return, this active hirudin can act on thrombin and inhibits its activity. The released active hirudin does not contain any amino acids of the plasmin cleavage site.

As indicated herein, this consensus sequence is recognized and cleaved efficiently by plasmin. In addition, this consensus sequence also renders the sequestered hirudin available and active to cleave thrombin. The preferred plasmin cleavage site used in the chimeras has the following consensus sequence:

$NH_2$-$X_1$-$X_2$-$X_3$-$X_4$-$X_5$-$X_6$-COOH (SEQ ID NO: 21)

In this consensus sequence, $X_1$, $X_2$ and $X_5$ can be the same or different amino acids. $X_1$, $X_2$ and $X_5$ are selected from an uncharged polar amino acid, such as, asparagine, asparagic acid, glycine, glutamine, glutamic acid, serine, threonine, tryptophan and tyrosine. In an embodiment, $X_1$ is a glycine residue, $X_2$ is a serine residue and/or $X_5$ is a serine residue or a tyrosine residue. Further, $X_3$ can be an hydrophobic amino acid (e.g. alanine, cysteine, phenylalanine, isoleucine, leucine, methionine, praline or valine) or an uncharged polar amino acid (e.g. those listed above). $X_3$ can be, for example, an alanine residue or a glycine residue. In addition, $X_4$ can be an hydrophobic amino acid (e.g. those listed above). $X_4$ can be, such as, for example, a methionine residue or an isoleucine residue. In addition, $X_6$ can be a basic hydrophilic amino acid (e.g. histidine, lysine, arginine or methylated arginine), such as arginine or lysine.

Specific embodiments of the plasmin cleavage site include, but are not limited to, the sequences set forth in SEQ ID NO: 7 or SEQ ID NO: 13.

As shown herein, the consensus sequence can be made up of naturally occurring L-amino acids. However, to prevent proteolytic cleavage or to optimize stability of the chimeric hirudin protein, the consensus sequence can also contain one or more D-amino acids or other non-natural amino acids. In such embodiment, the chimeric hirudin protein containing D-amino acids could be linked to a synthetic peptide or a liposome as a carrier.

When plasmin contacts the chimeric hirudin protein, it is believed that it cleaves the chimera between the $X_6$ residue of the plasmin cleavage site and the hirudin.

The chimeric hirudin protein comprises a third component, namely hirudin. As indicated above, hirudin is the most potent natural inhibitor of thrombin. A key event in the final stages of blood coagulation is the conversion of fibrinogen into fibrin by the serine protease enzyme thrombin. Thrombin is produced from prothrombin, by the action of an enzyme, prothrombinase, in the final states of coagulation. Fibrin is then cross-linked by factor XIIIa to form a blood clot. The principal inhibitor of thrombin in normal human blood circulation is antithrombin III. Similar to antithrombin III, the anticoagulant activity of hirudin is based on its ability to inhibit the pro-coagulant activity of thrombin. However, unlike antithrombin III, which requires heparin or heparan sulfate for maximal activity, hirudin does not require any other cofactor. Moreover, hirudin's ability to inhibit thrombin is not impaired when thrombin is present bound to a clot, as is the case for antithrombin III. Because clot growth or re-growth is a balance between clot formation and clot dissolution, hirudin can exert an indirect thrombolytic effect by preventing clot growth and allowing clot dissolution to proceed at a more rapid rate. In some aspects, hirudin has advantages over more commonly used anticoagulants and thrombolytics, such as heparin, as it does not interfere with the biological activity of other serum proteins and can also act on clot-bound thrombin.

Hirudin can be obtained from *Hirudinaria manillensis* (GenBank Accession Number CAA51293), *Hirudo medicinalis* (GenBank Accession Number CAA01205), *Poecilobdella viridis* (GenBank Accession Number P84590) or from recombinant technology (see for example, GenBank Accession Number CAA02181). Wild-type hirudin is organised into a compact N-terminal domain containing three disulfide bonds and a C-terminal domain which is disordered, when the protein is un-complexed in solution.

Wild-type hirudin from *Hirudo medicinalis* contains a mixture of various isoforms (HV1, HV2 and HV3) of the protein. HV1 and HV2 consist of a single polypeptide chain of 65 amino acids in which the $NH_2$-terminal apolar core and the strongly acid COOH-terminal tail bind to the apolar binding site and to the anion binding exosite of thrombin, thus preventing it from interaction with the substrate (fibrinogen). In addition, in position 63, a sulfated tyrosine is present; this post-translational modification does not appear to be essential for antithrombin activity. The sulfotyrosine is not essential but natural hirudins are about 10 times more powerful than recombinant forms because they have this feature. HV3 is identical to HV2 from positions 1 to 32 and then differs from HV1 in the following respects: Gln at position 33 instead of Asp, Lys at position 35 instead of Glu, Asp at position 36 instead of Lys, Gln at position 53 instead of Asp, Pro at position 58 instead of Glu, Asp at position 62 instead of Glu, Ala at position 63 instead of Tyr ($SO_3H$), Asp at position 64 instead of Leu and Glu at position 65 instead of Gln. The sequence of hirudin variant 3 is presented in the sequence listing (SEQ ID NO: 20) and can successfully be used in the chimeric hirudin protein presented herewith.

Hirudin is also available commercially in a number of hirudin-based anticoagulant pharmaceutical products such as Lepirudin (REFLUDAN®), hirudin derived from Hansenula (THROMBEX™, EXTRAUMA®) and Desirudin (REVASC™/IPRIVASK®).

According to another aspect, the present application also relates to a nucleic acid sequence coding for the chimeric hirudin protein described herein. Broadly, this nucleic acid comprises sequentially (i) a first sequence coding for the carrier operably linked (ii) a second sequence coding for the plasmin cleavage site and (iii) a third sequence coding for the hirudin. These three sequences are operably linked in the same open reading frame. This nucleic acid can also optionally comprise a promoter to facilitate or limit the expression of the chimeric hirudin protein. In another aspect, the present application also provides an expression cassette comprising the nucleic acid sequence defined herein. Broadly, the expression cassette is capable, under appropriate conditions, to express said chimeric hirudin protein. In a further aspect, the present application further provides a host cell comprising the nucleic acid of claim described herein or the expression cassette defined herein. The host cell is capable of expressing, under appropriate conditions, said chimeric hirudin protein. The expression "appropriate conditions" is intended to refer to conditions required for a host cell to grow and express the chimeric hirudin protein or conditions for the expression cassette to be translated to produce the chimeric protein. These conditions are known to one skilled in the art and will vary depending of the cassette constructed or the host cells used. A variety of host cells can be used for the expression of the hirudin chimeras. Such cells include, but are not limited to *Escherichia coli* and *Pichia pastoris*.

The isolated nucleic acid sequence, the expression cassette as well as the host cell can be used for the production of the chimeric hirudin protein. The isolated nucleic acid sequence, the expression cassette as well as the host cell can also be used for cell-based or gene-based therapy where a clot is linked to a disease.

According to yet to a further aspect, the chimeric hirudin protein can successfully be used as a thrombolytic agent (e.g. to dissolve a blood clot) or to prevent the formation of a blood clot.

As used herein, the term "thrombolysis" or "clot busting" refers to the breakdown or lysis of blood clots by pharmacological means. Formation of blood clots lies at the basis of a number of serious pathologies such as myocardial infarction, stroke (ischemic stroke), massive pulmonary embolism, and acute limb ischaemia. By breaking down the clot, the disease process can be arrested, or the complications reduced. Thrombolysis is usually intravenous. It may also be used during an angiogram (intra-arterial thrombolysis).

Thrombolysis requires the use of thrombolytic drugs currently known in the art, which are either derived from *Streptomyces* sp., or recombinant biotechnology. Some commonly used thrombolytics or thrombolytic agents include, but are not limited to streptokinase, urokinase, alteplase (rtPA), reteplase and tenecteplase.

In comparison to thrombolytic agents actively reduce the size of the clot, "anticoagulants" (such as heparin) decrease the "growth" of a clot, thrombolytic agents. Most of the thrombolytic agents currently used are administered together with an anticoagulation such as heparin (unfractionated or low molecular weight heparin), usually for 24-48 hours.

According to another aspect, the present application provides a method of limiting the growth of a clot in a subject in need thereof. Broadly, this method comprises the step of administering to the subject the chimeric hirudin protein as defined herein to prevent the formation or growth of said clot. As used herein "the prevention of the formation or the growth of a clot" refer to the ability of the chimeric hirudin protein to limit or stop the growth of a pre-existing blood clot. In an embodiment, the chimeric hirudin protein is administered with a thrombolytic agent or, optionally, after the thrombolytic agent.

According to a further aspect, the present application also provides a method for busting a clot in a subject in need thereof. Broadly, the method comprises the step of administering to the subject the chimeric hirudin protein as defined herein, to reduce the size of the clot. As used herein, the term "busting a clot" refer to the ability of the chimeric hirudin protein to reduce the size of the blood clot once the active hirudin moiety is released from the carrier and the plasmin cleavage site. In an embodiment, the chimeric hirudin protein is administered with a thrombolytic agent or, optionally, after the thrombolytic agent.

Also contemplated herein are the use of the chimeric hirudin protein for the prevention or the thrombolysis of a blood clot in a subject as well as for the manufacture of a medicament for the prevention or the thrombolysis of a blood clot in a subject. In an embodiment, the chimeric hirudin protein is formulated for administration with a thrombolytic agent.

Further contemplated herein, is a chimeric hirudin protein as described herein for use in the prevention or thrombolysis of a blood clot in a subject. In an embodiment, such chimeric hirudin protein can be formulated for administration with a thrombolytic agent.

The chimeric hirudin protein can be administered with an excipient. An excipient or "pharmaceutical excipient" is a pharmaceutically acceptable solvent, suspending agent or any other pharmacologically inert vehicle for delivering one or more chimeric hirudin protein to a subject, and is typically liquid. A pharmaceutical excipient is generally selected to provide for the desired bulk, consistency, etc., when combined with components of a given pharmaceutical composition, in view of the intended administration mode. Typical pharmaceutical excipients include, but are not limited to binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycotate, etc.); and wetting agents (e.g., sodium lauryl sulphate, etc.).

The chimeric hirudin protein may be administered with a pharmaceutically-acceptable excipient, in unit dosage form. Conventional pharmaceutical practice may be employed to provide suitable formulations or compositions to administer such compositions to subjects. Although intravenous administration is preferred, any appropriate route of administration may be employed, for example, oral, perenteral, subcutaneous, intramuscular, intracranial, intraorbital, ophthalmic, intraventricular, intracapsular, intraspinal, intrathecal, epidural, intracisternal, intraperitoneal, intranasal, or aerosol administration. Therapeutic formulations may be in the form of liquid solutions or suspension. Methods well known in the art for making formulations are found in, for example, Remington: The Science and Practice of Pharmacy, (19th ed.) ed. A. R. Gennaro A R., 1995, Mack Publishing Company, Easton, Pa.

In addition, the term "pharmaceutically effective amount" or "therapeutically effective amount" refers to an amount (dose) effective in treating a patient. It is also to be understood herein that a "pharmaceutically effective amount" may be interpreted as an amount giving a desired therapeutic effect, either taken in one dose or in any dosage or route, taken alone or in combination with other therapeutic agents.

A therapeutically effective amount or dosage of a chimeric hirudin protein disclosed herein or a pharmaceutical composition comprising the chimeras, may range from about 0.001 to 30 mg/kg body weight, with other ranges of the invention including about 0.01 to 25 mg/kg body weight, about 0.025 to 10 mg/kg body weight, about 0.3 to 20 mg/kg body weight, about 0.1 to 20 mg/kg body weight, about 1 to 10 mg/kg body weight, 2 to 9 mg/kg body weight, 3 to 8 mg/kg body weight, 4 to 7 mg/kg body weight, 5 to 6 mg/kg body weight, and 20 to 50 mg/kg body weight. In other embodiments, a therapeutically effective amount or dosage may range from about 0.001 to 50 mg total, with other ranges of the invention including about 0.01 to 10 mg, about 0.3 to 3 mg, about 3 to 10 mg, about 6 mg, about 9 mg, about 10 to 20 mg, about 20-30 mg, about 30 to 40 mg, and about 40 to 50 mg. In an embodiment, the hirudin chimera is administered to a dosage between about 40-80 mg/kg (e.g. 60 mg/kg). The hirudin chimeras can be about 9 times bigger than unfused wild-type hirudin.

In order to design a potent and useful chimeric hirudin protein, the N-terminal-hirudin was linked to a C-terminal carrier protein and a plasmin cleavage site that would yield a plasmin-activatable hirudin molecule were created. Several potential plasmin cleavage sites were first compared using the fusion partner glutathione sulfotransferase (GST). This protein is robustly expressed in *E. coli*; in contrast, the 17 disulphide bonds, and single unpaired cysteine residue in human serum albumin (HSA) has been an original dissuasion from attempting expression of an even more complex fusion protein, which would also contain the three obligatory disulphide bonds in its huridin variant HV3 moiety used, in the reducing environment found within bacteria.

Three potential plasmin cleavage sites cle1, cle2, and cle3 were screened. Although the GSTcleXHV3 fusion proteins contained the same $P_6$-$P_1$ residues as in the case of these sequences, expressed both in the context of phage coat protein III and in that of staphylococcal nuclease, the residues C-terminal to the scissile bond differed (ITY versus SRS) in the present constructs. The cleavage sequences were not susceptible to non-specific proteolysis in *E. coli*, or for that matter to cleavage by another serine protease, thrombin, but instead were activated specifically by plasmin in the GST fusion context. This property proved transferable, from the C-terminus of GST to that of HSA (human serum albumin) or AGP (alpha-1-acid glycoprotein) as well as other carrier protein, as shown by the similar specificity with which the HSA-based chimera was activated by plasmin, compared to the same sequence in GST-based chimeras.

Because of the potential utility of an albumin fusion protein in the mammalian circulation, the properties of HSA-based chimeras were then investigated more thoroughly than those of GST-based chimeras. HSA-based chimera was efficiently expressed in the *Pichia pastoris* methylotropic yeast expression system.

As expected for a bona fide plasmin substrate, HSA-based chimera was cleaved in a time- and concentration-dependent manner, both with respect to its own concentration and that of plasmin. Although the C-terminal dodecapeptide of hirudin has been shown to be capable of inhibiting thrombin-mediated cleavage of fibrinogen, its presence in control, non-activatable fusion protein HSAHV3 was insufficient to inhibit thrombin under the conditions employed in our hands.

An attractive property of direct thrombin inhibitors such as hirudin is their ability to inhibit clot-bound thrombin. As expected for an activatable protein designed to liberate hirudin variant 3 (HV3), which should in all respects be identical to its unfused counterpart, HSA-based chimera (HSACHV3) inhibited the clot-bound thrombin that was solely responsible for clot growth in the discontinuous assay that was employed, when nanomolar concentrations of tissue-type plasminogen activator (tPA) were provided. While no direct effect of HSACHV3 or liberated hirudin on fibrinolysis was expected or demonstrated, clot lysis was enhanced due to inhibition of clot extension by hirudin. The relevance of this observation was supported by its replication in the plasma system, albeit at higher concentrations necessitated by the presence of both higher concentrations of fibrinogen and inhibitors of coagulation and fibrinolysis in plasma. In both instances, the release of only a small portion of the total available HV3 contained within HSACHV3 was required for maximal clot lysis, proving the utility of this chimeric protein, in situations in which it could provide a slowly cleared reservoir of safely latent hirudin.

The chief obstacle to more effective exploitation of hirudin as an antithrombotic agent is its property of increasing bleeding. As shown herein, a mouse tail transaction model highly similar to that employed by Zhang et al., in their recent study of latent hirudins with 3-5 amino acid extensions (Zhang C, Yu A, Yuan B, et al., Thromb Haemost 2008; 99: 324-330) was used. Interestingly, at doses of these modified hirudins of 6 mg/kg, significant elevations of mouse tail bleeding times were reported relative to saline-infused controls. At highly similar molar doses of the much larger protein HSACHV3, no increase in blood loss was observed under conditions in which a significant, 4-fold elevation of blood loss was elicited by HV3 administration. This dichotomy suggests that either higher concentrations of procoagulant factors such as thrombin and factors Xa and XIa, to which the minimally modified EH, GH, and LH hirudins are susceptible, are generated in the murine tail transection injury than plasmin, or that the much larger HSA domain is a more effective insulator of hirudin activation that the shorter sequences.

Another potential advantage of the HSA fusion approach is the slow clearance profile of HSACHV3 demonstrated in this study in mice. Our observations with respect to the enhanced durability of the pharmacodynamic effects of hirudin-albumin fusion proteins in a rabbit model of arterial prothrombotic injury prove transferable to the novel configuration employed in HSACHV3, such that a prolonged duration of action of this protein is observed in vivo. These findings suggest a possible application in which HSACHV3 provides a circulating reservoir of latent hirudin, one that is activated only in thrombi undergoing digestion by plasmin, either via endogenous processes or in response to thrombolytic therapy. The results in this study, with respect to the ability of HSACHV3 to respond specifically to plasmin in both purified and plasma in vitro systems, coupled with the clear lack of promotion of hemorrhage by this novel albumin chimera, and the demonstration of its pharmacokinetics, suggested the appropriateness of examining this issue in animal models. This approach has the potential to improve the utility of hirudin as an adjunctive anticoagulant for clinical benefit. An improved adjunctive agent such as the one described herein in thrombolytic therapy could provide improvements proposed for thrombolytic agents themselves, specifically selectivity for thrombi, reduced recurrence of vascular blockages, long half-life, and a reduced bleeding diathesis.

Similar findings were obtained by swapping the HSA carrier with a AGP carrier. AGP or orosomucoid is a smaller protein than HSA (41 to 43 kDa) and is heavily glycosylated. When AGP is linked to a plasmin cleavage site and ultimately to hirudin, it inhibits hirudin endopeptidic activity. However, in the presence of plasmin, hirudin is released from the carrier and can act to lower thrombin's activity.

The present invention will be more readily understood by referring to the following examples which are given to illustrate the invention rather than to limit its scope.

EXAMPLE I

Construction and Characterization of GST-Based Chimeras

Nucleic Acid Constructs.

In order to adapt glutathione sulfotransferase (GST) for use as a fusion protein, pGEX5X-1 was first modified by PCR to remove a factor Xa cleavage site from the modified GST encoded by this commercial vector. PCR employed heat-stable DNA polymerase ThermalAce™ (Invitrogen, Carlsbad, Calif.) and oligonucleotides synthesized by the MOBIX Lab central facility of McMaster University. The GST cDNA was modified by PCR using oligonucleotide primers ML3205 (5'-CTGGCTGGAG TGCGATCTTC CTGAGGC-3', SEQ ID NO: 1) and ML3206 (5'-GCCGCTCGAG TACGTACCAT GGATCCCAGA TCCGATTTTG GAGGATG-3', SEQ ID NO: 2), the PCR product restricted with Bsu36I and XhoI, and the 1145 by restriction digestion fragment inserted between the corresponding sites of pGEX5X-1, to form plasmid pGEX5-VB. Next, a previously described hirudin variant 3 (HV3) cDNA was PCR-amplified from a pPIC9HLA template (Syed S, Schuyler P D, Kulczycky M, et al., Blood 1997; 89: 3243-3252) using oligonucleotide primers ML3207 (5'-GTATTACGTA CACAGACTGC ACAGAGTCTG GCCAG-3', SEQ ID NO: 3) and ML3208 (5'-ATGCGGCC GCTACTCATC ATAGGCATCC TCAG-3', SEQ ID NO: 4). The resulting PCR product was restricted with SnaBI and NotI, and the 197 by restriction fragment was inserted between the corresponding sites of pGEX5-VB to form plasmid pGEXHV3. Cassette mutagenesis was then used to position each of three plasmin cleavage sites (cle1 (SEQ ID NO: 7), cle2 (SEQ ID NO: 10) and cle3 (SEQ ID NO: 13)) between the GST and HV3 cDNAs, by annealing pairs of oligonucleotides and inserting them between the BamHI and SnaBI sites of pGEXHV3. The pairs were: ML3209 (5'-GATCCGGTTC TGCAATGTCT CGTATTAC-3', SEQ ID NO: 5) and ML3210 (5'-GTAATACGAG ACATTGCAGA ACCG-3', SEQ ID NO: 6) encoding del, GSAMSR (SEQ ID NO: 7); ML3213 (5'-GATCCAAAAA GTCTCCTGGA CGTATTAC-3', SEQ ID NO: 8) and ML3214 (5'-GTAATACGTC CAGGAGACTT TTTG-3', SEQ ID NO: 9) encoding cle2, KKSPGR (SEQ ID NO:10); and ML3211 (5'-GATCCGGCTC TGGAATCTAT CGTATTAC-3', SEQ ID NO: 11) and ML3212 (5'-GTAATACG ATAGATTCCA GAGCCG-3', SEQ ID NO: 12) encoding cle3, GSGIYR (SEQ ID NO: 13). These plasmids, as well as all other plasmids encoding recombinant proteins used in this experiment, were subjected to confirmatory DNA sequencing by MOBIX Lab prior to use in any protein expression experiments.

Selection of Plasmin Cleavage Site.

The plasmin cleavage site was first sought for positioning N-terminal to hirudin, mindful of the requirement that $Ile_1$ of HV3 be precisely positioned as the new N-terminus of the proteolytically liberated hirudin. Three sequences (see FIG. 1A): GSAMSR (SEQ ID NO: 7); KKSPGR (SEQ ID NO: 10); and GSGIYR (SEQ ID NO: 13) were tested. The first (del) corresponds to the 6 residues N-terminal to the scissile bond in α2-antiplasmin ($P_6$-$P_1$ using the Schechter and Berger nomenclature in which Px residues are N-terminal and Px' C-terminal to the scissile bond). The second (cle2) corresponds to a plasmin activation site in microplasmin. The third (cle 3) was selected in a phage display substrate optimization study, which also tested the other two sequences (Hervio L S, Coombs G S, Bergstrom R C, et al. Chem Biol 2000; 7: 443-53). In FIG. 1A, the hexameric sequences tested for recognition by plasmin are shown below the bracket, where plasmin cleavage to release HV3 with an authentic $Ile_1$ N-terminus was predicted C-terminal to the common R residue. Amino acid residues forming the boundary of the different components of the fusion proteins are shown above the linear diagrams.

Expression, Purification, and Characterization of GST-HV3 Fusion Proteins.

Figure 1B:
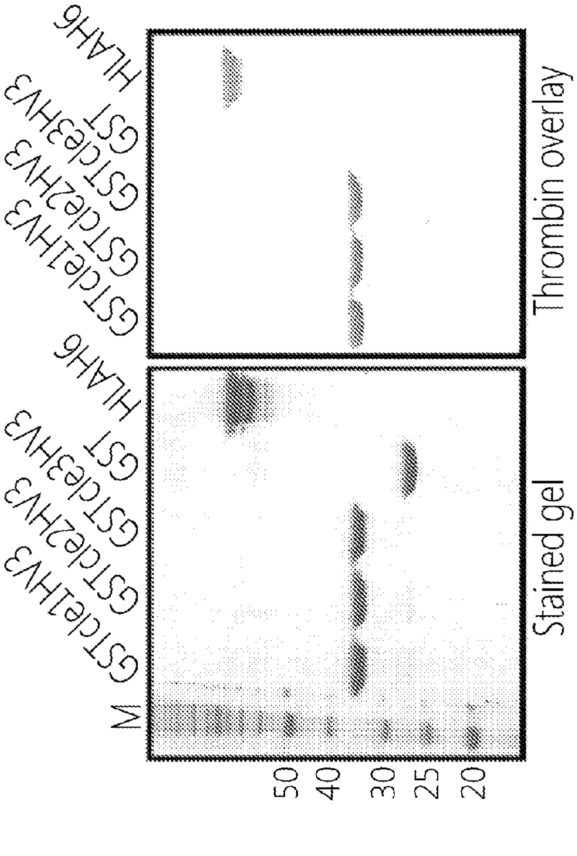

The pGEX-cleX-HV3 plasmids were separately used to transform *E. coil* BL21 to ampicillin resistance. Clonal cultures were grown in Luria Broth supplemented with ampicillin to 0.5 $OD_{600}$ absorbance units per ml, induced with 0.1 mM isopropylthiogalactoside (IPTG) for 3 hours, and cells harvested by centrifugation. GST proteins were purified from sonicated lysates as described in Cunningham (Cunningham M A, et al., Thromb. Haemost. 2002; 88: 89-97), except that a single step of glutathione-agarose affinity purification, under conditions specified by the manufacturer (Sigma-Aldrich, Mississauga, Ontario), was sufficient for purification to near-homogeneity. All three, in the context of GSTcleXHV3 fusion proteins, were abundantly expressed as soluble proteins in *E. coli*, and purified to similar near-homogeneous levels, as shown in FIG. 1B. Thrombin blot overlays were performed on nitrocellulose essentially as described by Syed et al. (Syed S, et al., Blood 1997; 89: 3243-3252), using human α-thrombin (Enzyme Research Laboratories, South Bend, Ind., [ERL]) at 4 mg/ml, anti-thrombin-horse radish peroxidase conjugate (Affinity Biologicals, Ancaster, Ontario) at 1:2,000, and diaminobenzamidine substrate. Unless otherwise noted, reactions of HV3 fusion proteins with plasmin or thrombin were performed in PPNE buffer (20 mM sodium phosphate pH 7.4, 100 mM NaCl, 0.1 mM EDTA and 0.1% w/vol polyethylene glycol). To test activation of GSTcleXHV3 proteins, a two-stage assay was employed in which 15 μM GSTcleXHV3 was incubated with 75 nM plasmin at 37° C. At various times, aliquots were combined with an equal volume of 100 units/ml aprotinin (Trasylol; Bayer Healthcare, Etobicoke, Ontario) to inhibit plasmin (ERL), diluted ten-fold, combined with an equal volume of 14 nM thrombin for one minute, then further diluted 10-fold into 100 μM S2238 chromogenic substrate (Chromogenix, Lexington, Mass.). Colour development was monitored for 5 minutes in an ELx808™ plate reader (BioTek Instruments, Winooski, Vt.) at 405 nm, and the velocity of amidolytic reaction was measured. As shown on FIG. 1B, the GST chimeras as well as the polyhistidine-hirudin appear distinctly on the thrombin overlay. The velocity of the uninhibited reaction was set to 100%. Some reactions were analyzed electrophoretically on SDS polyacrylamide gels, which were in all instances run under reducing conditions.

Figure 1C:
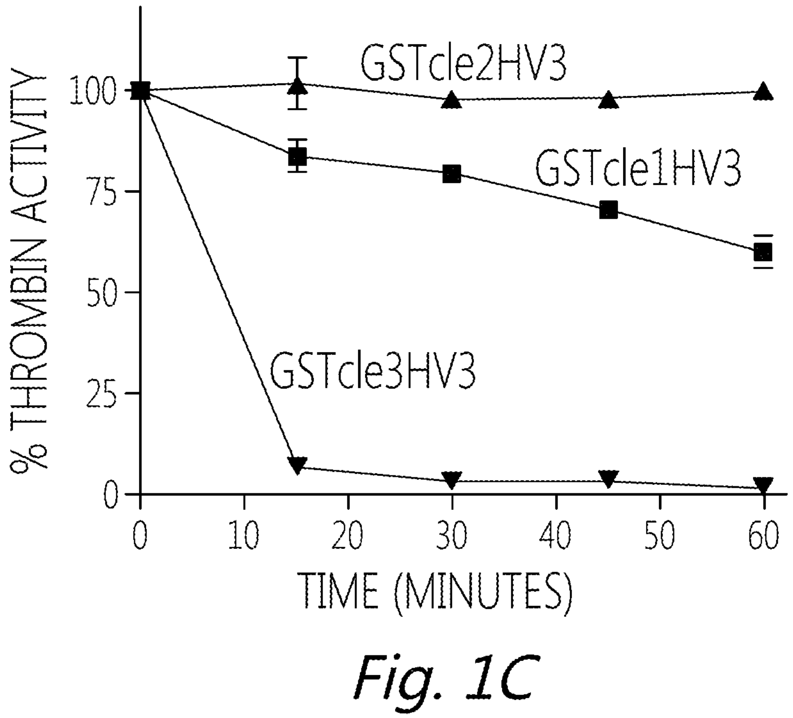
Figure 1D:
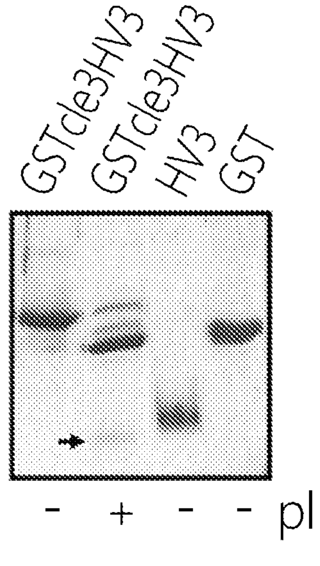

The three GST-hirudin fusion proteins were screened for the ability to become activated by plasmin, when present in equal, 20-fold molar excess over the protease. None of the fusion proteins showed any evidence of thrombin inhibitory activity in the absence of plasmin activation. Surprisingly, in spite of the cle2 sequence being recognized and cleaved by plasmin when present in α2-antiplasmin, a highly effective natural plasmin inhibitor, GSTcle2HV3 exhibited little or no generation of thrombin inhibitory activity, whereas a detectable evolution of thrombin inhibitory activity was apparent over the 60 minutes of the experiment for GSTcle1HV3 (FIG. 1C). In FIG. 1C, data are the mean of two measurements±the range. GSTcle3HV3, in contrast, was rapidly activated and inhibited all thrombin present in the assay. Because of the reaction conditions selected, this was not necessarily indicative of the reaction going to completion. To clarify this point, a similar but lengthier activation experiment was carried out at 10-fold molar excess of plasmin over fusion protein, and the cleavage pattern examined by SDS-PAGE. As shown in FIG. 1D, plasmin-dependent polypeptide species were detected, one of which co-migrated with unfused GST, and the other, which migrated slightly more rapidly than *Pichia pastoris*-derived recombinant hexahisitidinylated HV3. The difference might have arisen due to the absence of hexahistidines on the released HV3 compared to the marker.

EXAMPLE II

Construction and Characterization of Albumin-Based Chimeras

Nucleic Acid Constructs.

The human serum albumin (HSA) cDNA was manipulated for expression as a C-terminally hexahistidine-tagged *Pichia pastoris* expression product by PCR amplification, using heat-stable DNA polymerase Phusion™ (New England Biolabs, Ipswich, Mass.) and oligonucleotides ML12007 (5'-CATGGAATTC TTAATGGTGA CGGTGATGGT GTAAGCCTAA GGCAGCTCGA CTTGCAGCAA C-3' (SEQ ID NO: 14)) and ML12008 (5'-GATCCTCGAG AAAAGAGACG CACACAAGAG TGAGGTTGC-3' (SEQ ID NO: 15)). The resulting 1788 by amplification product was restricted with XhoI and EcoRI and inserted between these sites in pPICZ9ssamp (Sheffield W P, et al., Blood Coagul Fibrinolysis 2001; 12: 433-443) to form pPICZ9ssHSAH$_6$. This plasmid served as the template for PCR with oligonucleotide primers ML12589 (5'-CAGAGGCTCA AGTGTGCCAG-3', SEQ ID N: 16) and ML 12910 (5'-AGCTGGATCCT AAGGCAGCTC GACTTGCAG-3', SEQ ID NO: 17). This PCR product was restricted with XbaI and BamHI, and the 682 by restriction fragment was ligated to the 225 by pGEXcle3HV3 BamHI-NotI fragment and inserted between XbaI and NotI sites of pPICZ9ssHSAH$_6$. The resulting plasmid was designated pPICZ9ssHSACHV3. Next, unfused hexahistidinylated HV3 expression was enabled by mobilization of the HV3 codons in pGEXcle3HV3 using oligonucleotides 5'-GCTTTCTCG AGAAAAGAAT TACGTACACA GACTGCAC-3' (SEQ ID NO: 18) and 5'-GCATGGCGGC CGCCCTAGTG GTGATGATGG TGGTGCTCAT CATAGGCATC CTCAG-3' (SEQ ID NO: 19), restriction of the product with XhoI and NotI, and insertion of the 253 by fragment between these sites of pPICZ9ssamp to form pPICZ9ssHV3H$_6$. Finally, the XhoI-Bst1101I fragment of pPICZ9ssHV3H$_6$ was replaced with the corresponding fragment of pPICZ9ssHSACHV3, forming pPICZ9ssHSACHV3H$_6$. Plasmid pPICZ9ssHSAHV3H$_6$ was created using analogous methods, and differed from pPICZ9ssHSACHV3H$_6$ only in lacking 18 by encoding hexapeptide GSGIYR (SEQ ID NO: 13) plasmin cleavage site between the HSA- and HV3-encoding nucleotides of the former plasmid.

Expression in *Pichia pastoris*.

Figure 2A:
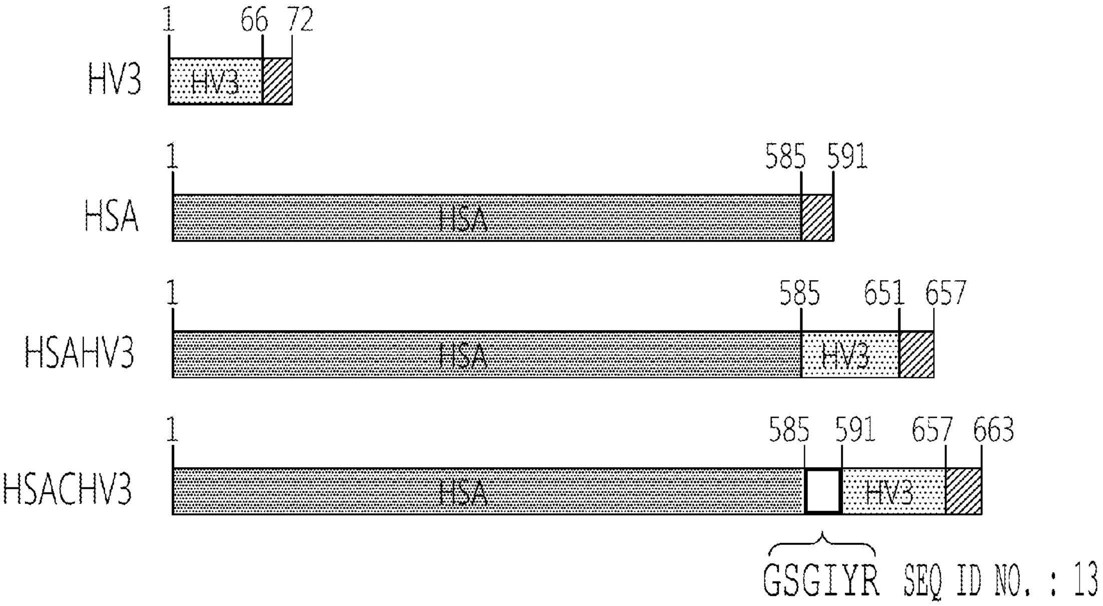
FIG. 2 Serum albumin fusion proteins. (A) illustrates a schematic diagram ($NH_2$ to COOH) of C-terminally His-tagged hirudin variant 3 (HV3), human serum albumin, a human serum albumin and hirudin variant 3 fusion protein without a plasmin cleavage site (HSAHV3) and a human serum albumin and hirudin variant 3 fusion protein with a plasmin cleavage site (HSACHV3 having the plasmin cleavage site of SEQ ID NO: 13) in linear form. (B) illustrates Coomassie Blue-stained 8% SDS-polyacrylamide gels of HSACHV3 and HSA constructs expressed in *Pichia pastoris* yeast and purified by nickel-chelate affinity chromatography (2.0 µg per lane). (C) illustrates the reaction of either unlabelled HSACHV3 on the portion of the stained gel shown in the upper panel (gel), or of radioiodinated $^{125}$I-HSACHV3 (detected on autoradiograms (A/R) of 12% SDS polyacrylamide or 16.5% Tris-Tricine SDS-polyacrylamide gels.
Figure 2B:
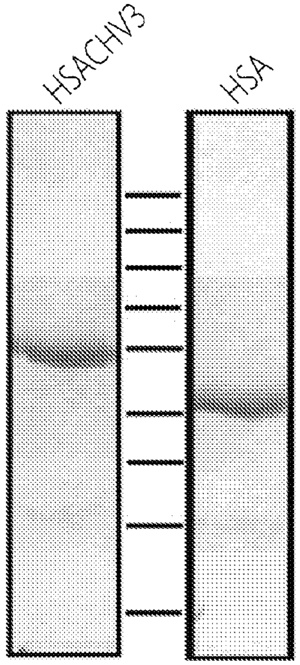

The GSGIYR cle3 site (SEQ ID NO: 13), selected on the basis of its behavior in the bacterial GST-HV3 fusion protein, was re-expressed in an albumin-hirudin chimera, and appropriate expression plasmids were constructed and transferred to *Pichia pastoris* yeast for expression as secreted proteins. Unlike previous albumin fusion proteins produced, these proteins made use of the human serum albumin (HSA) form, as shown schematically in FIG. 2A. For ease of comparison, and to enable use of essentially the same protein purification scheme, a hexahistidine tag was appended to all yeast-derived recombinant products, listed with their calculated molecular weights in daltons; recombinant HV3, 7,848; recombinant HSA, 67,293; recombinant HSAHV3, a seamless fusion of the terminal $S_{585}$ residue in HSA to $I_1$ in HV3, 74,274; and HSACHV3, HSAHV3 with GSGIYR (SEQ ID NO: 13) inserted between HSA $Ser_{585}$ and $I_1$ in HV3, 74,908. In FIG. 2A, grey bars depict HV3 sequences, and stippled zones correspond to hexahistidine sequences, while black bars are HSA domains. The hexameric plasmin cleavage site of HSACHV3 is shown as a white bar. Proteins were purified using nickel-chelate affinity chromatography to >95% homogeneity, as judged by densitometry of stained gels; importantly, no evidence of cleavage of HSACHV3 to an HSA-sized polypeptide was observed (FIG. 2B, compare left and right panels). In FIG. 2B, markers, between the lanes, correspond to 200, 150, 120, 100, 85, 70, 60, 50 and 40 kiloDaltons, from top to bottom, respectively. Recombinant HSA migrated near commercial 70 kDa markers, while HSACHV3 migrated near 85 kDa. The latter observation was highly similar to previous findings with HLAH6, which was shown by mass spectrometry to possess a 74.5 kDa mass in spite of its migrating less rapidly than an 80 kDa marker.

All constructs described above in the pPICZ9ssamp background were purified using commercial DNA preparation columns (Qiagen, Chatsworth, Calif.), linearized with SacI, and used to transform *Pichia pastoris* yeast cells to Zeocin (Invitrogen) resistance. Recombinant proteins were purified from media conditioned by clonal transformed cell lines induced with 0.5% vol/vol methanol. Briefly, media were neutralized, separated from cells by centrifugation, concentrated by diafiltration, made 0.1 mM in phenylmethylsulfonyl fluoride (PMSF), 5 mM in benzamidine and 0.2% in sodium azide, and purified using Ni-NTA agarose (Qiagen) as described, with the only difference being that recombinant HV3 was not concentrated prior to chromatography due to its small molecular weight (7848 Da). Typical yields for preparations of recombinant HSA, HSAHV3, or HSACHV3 ranged from 25-40 mg/L of conditioned media for shaker flask cultures, and yields of HV3, on a molar basis, were similar.

Characterization of the Cleavage by Plasmin of the Various Chimeras.

Figure 2C:
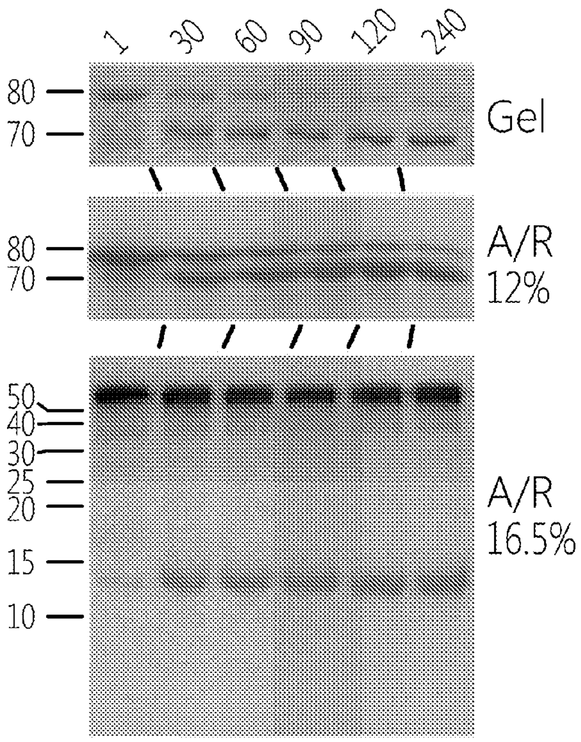

Purified HSACHV3 was next reacted with plasmin. Purified HSACHV3 or HSAHV3 fusion proteins were reacted with plasmin and thrombin using conditions described above for GSTcleXHV3 bacterial expression products. In some reactions, the HSACHV3 protein was radioiodinated using sodium iodide ($^{125}$I) by the Iodogen method as directed by the manufacturer (Thermo Scientific Pierce, Rockford, Ill.), and separated from unbound $^{125}$I by exhaustive dialysis. Specific activities of labeling were between 0.2-1.0×10$^8$ cpm/mg. Reaction products of plasmin digestion were analyzed by SDS-PAGE or by using autoradiography of dried gels. As shown in the upper panel of FIG. 2C, HSACHV3 was cleaved by plasmin over time, reaching near complete conversion. Because of the large difference in mobility between the major and minor (HV3) digestion products, HSACHV3 was radiolabeled with $^{125}$I and reaction products re-examined by autoradiography of dried gels. The kinetics of cleavage were largely unaffected by iodination (compare upper and middle panel). Electrophoresis on 16.5% Tris-Tricine gels (FIG. 2C, lower panel) allowed visualization of liberated hirudin, which increased over time and co-migrated with unlabeled HV3. Both the digestion product and the purified HV3 migrated much less rapidly than would be predicted from their molecular mass, suggesting that the aberrant migration of HSACHV3 arises from the hirudin domain. The size of the liberated thrombin was consistent with the extent to which uncleaved HSACHV3 migration lagged behind that of HSA in FIG. 2B. In FIG. 2C, markers, in kDa, are shown at left.

Clot Bound Thrombin Assay.

In order to test the ability of fusion protein HSACHV3 to inhibit clot bound thrombin, a discontinuous clot formation/clot lysis assay was employed. Clotting was initiated by the addition of thrombin to 5 nM final concentration to Tris-buffered saline (TBS) containing 0.5 μM Glu-plasminogen, 3 μM fibrinogen, and 50 nM factor XIII. All proteins were of human origin and were purchased from ERL. Total reaction volume was 0.15 ml in microtiter plate wells. After 30 minutes at 25° C., clots were removed from the well with fine forceps, washed three times in TBS, and transferred to a new reaction well containing 0.1 ml of 6 μM fibrinogen with or without 1.0 nM tissue-type plasminogen activator (single chain recombinant tPA, carrier-free, from Genentech (South San Francisco, Calif.), in the presence of purified HSACHV3 in concentrations ranging from 0 to 33 nM, in TBS supplemented with 2 mM $CaCl_2$. The turbidity associated with the secondary clot was monitored for 4 hours at 25° C. in a plate reader set to record the $OD_{340}$ every 30 seconds. In some reactions HSACHV3 was pre-activated with plasmin and the plasmin inactivated with aprotinin, as described above.

Figure 3A:
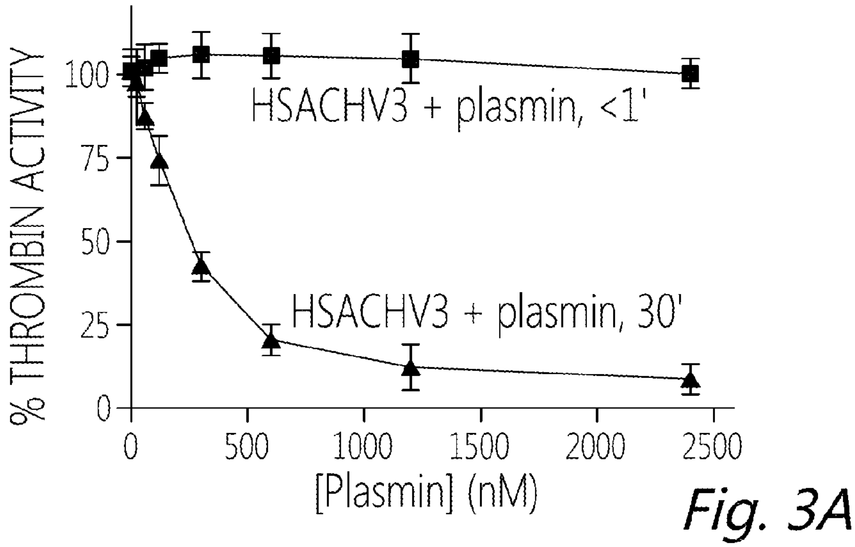
FIG. 3 illustrates the effects of plasmin or HSACHV3 concentration or time on the liberation of thrombin inhibitory activity. (A) HSACHV3 concentration was fixed at 376 nM and plasmin concentration was varied. Plasmin was either added as rapidly as possible (plasmin <1') or 30 minutes after the addition of HSACHV3. Results are shown as percentage of thrombin inhibitory activity in function of plasmin concentration (nM). (B) Plasmin concentration was fixed at 600 nM. Plasmin was either added as rapidly as possible (plasmin <1') or 30 minutes after the addition of HSACHV3. Results are shown as percentage of thrombin inhibitory activity in function of HSACHV3 concentration (nM). For comparison, the open bar represents a mock reaction carried out for 125 minutes without plasmin (C) Plasmin concentration was fixed at 600 nM. HSACHV3 concentration was fixed at 376 nM HSACHV3. Results are shown as percentage of thrombin inhibitory activity in function of time (minutes). The open bar represents a mock reaction lacking plasmin carried out for 125 minutes.
Figure 3B:
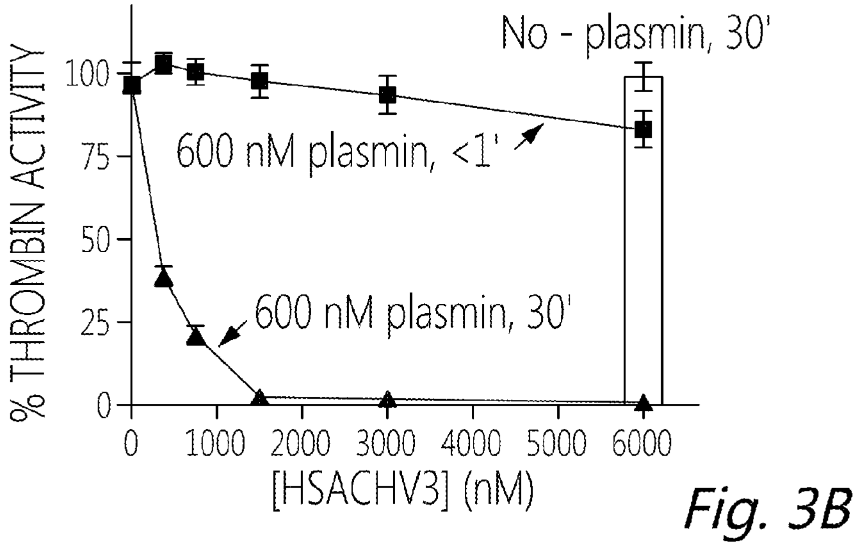
Figure 3C:
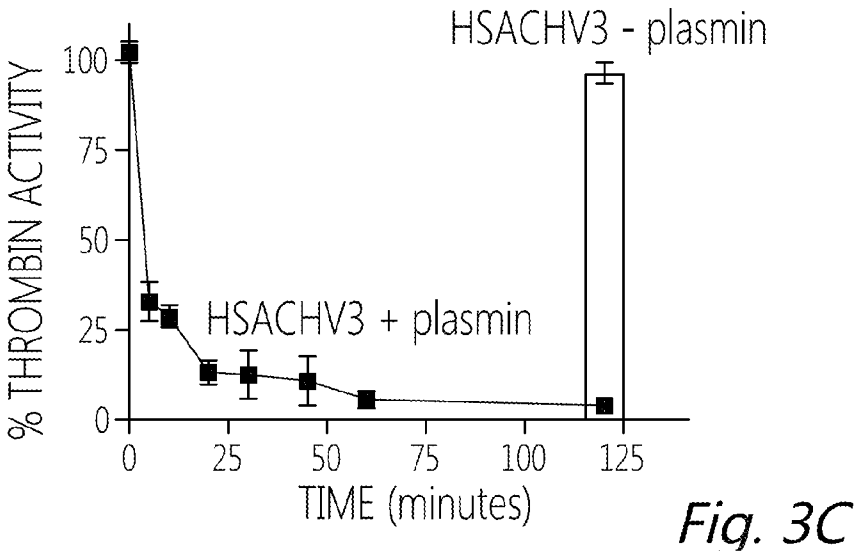

It was sought to confirm that the latency of HV3 activity observed with GSTcle3HV3 had been reproduced with HSACHV3. A variety of conditions, including excesses of protease (plasmin) over substrate (HSACHV3) unlikely to occur following cleavage of the chimeric protein in vivo were deliberately sampled, to test the limits of the latency of HV3 liberation. Exposure of the fusion protein to plasmin, followed by immediate inhibition of plasmin with aprotinin, released no detectable HV3, even at 7-8-fold molar excesses for 30 minutes (FIG. 3A). In FIG. 3A, squares represent reactions initiated and terminated as rapidly as possible in under one minute (<1'), while inverted triangles represent 30 minute reactions. Similarly, HSACHV3 was fully stable in the absence of plasmin (see bars in FIGS. 3B and 3C). In FIG. 3B, the open bar represents a mock reaction lacking plasmin. Increasing either the plasmin concentration at fixed HSACHV3 or the HSACHV3 concentration at fixed plasmin concentration led to increased release of HV3 and inhibition of thrombin; similarly, the release of thrombin was time-dependent. In contrast, under all conditions sampled in the experiments shown in FIG. 3, thrombin inhibition was unaffected by the presence of HSAHV3 following reaction with plasmin. In FIGS. 3A to 3C, purified HSACHV3 was incubated with plasmin as described herein. At selected times, plasmin cleavage was stopped by addition of aprotinin and the velocity of thrombin-mediated chromogenic substrate reactions was determined and expressed relative to uninhibited controls (% THROMBIN ACTIVITY). All data points are the mean of 8 replicates±SD.

Continuous Assay of Clot Formation and Lysis.

Normal human pooled plasma anticoagulated with citrate-phosphate-dextrose (CP2D) was purchased from Innovative Research (Southfield, Mich.) and 50 μl was combined with an equal volume of TBS containing 2 mM $CaCl_2$, and 0.5 nM tPA, and clotting was initiated by the addition of thrombin in 25 μl to give 5 nM final concentration. Reactions were carried out in microtiter plate wells continuously monitored for turbidity as described above.

Figure 4A:
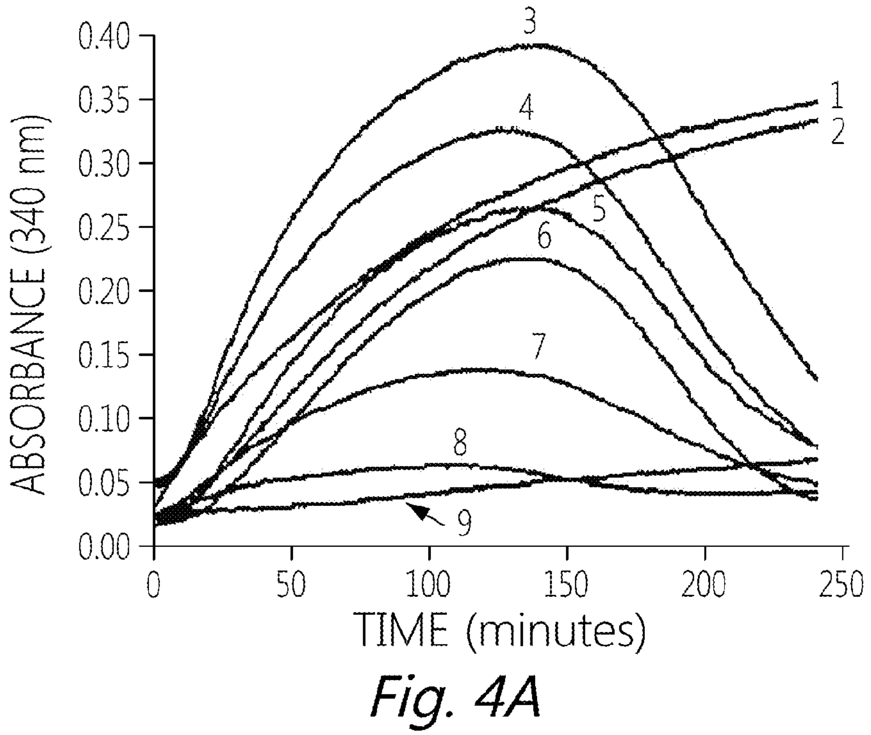
FIG. 4 illustrates the effects of HSACHV3 on clot extension and lysis by clot-bound thrombin. (A) depicts the change in turbidity (absorbance at 340 nm) over time (in minutes) caused by transfer of a washed, cross-linked fibrin clot into a reaction mixture containing fibrinogen and Glu-plasminogen in Tris-buffered saline supplemented with calcium chloride. (B) shows the area under the turbidity curve (AUC), in arbitrary units directly related to the product of absorbance and time, for a total of 5 experiments ±SD. * shows a statistically significant result.
Figure 4B:
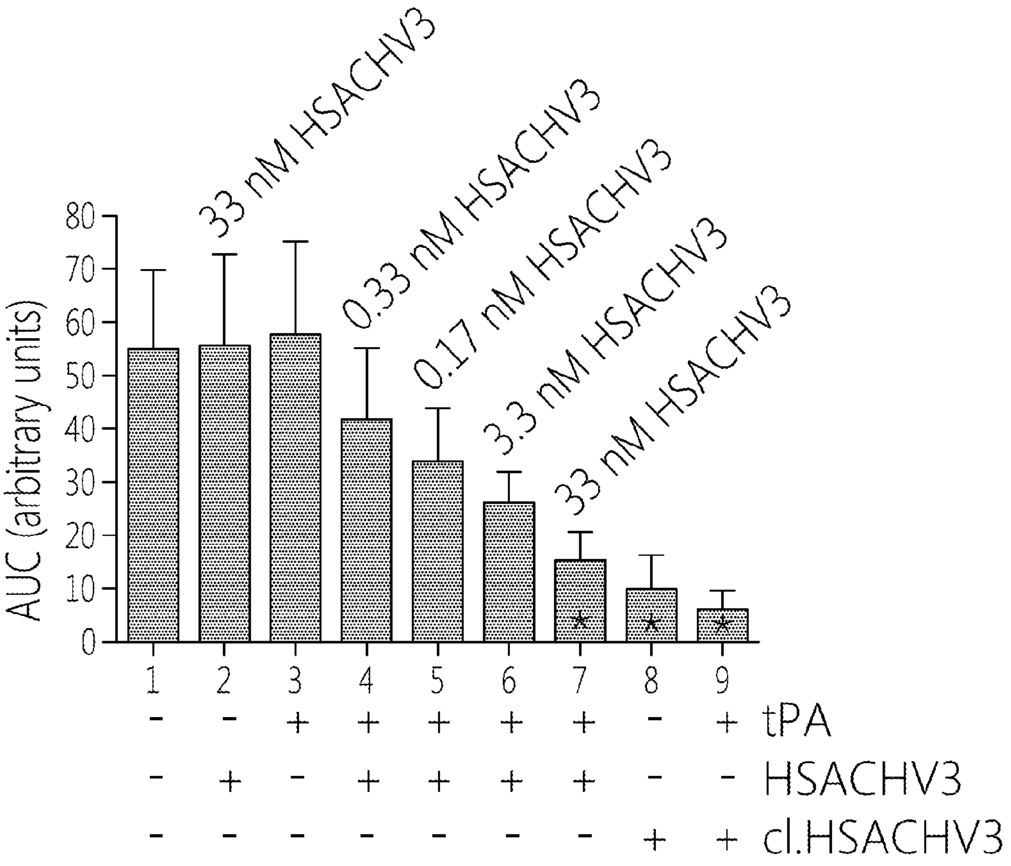

The complexity of the reaction milieu of HSACHV3 was then increased, using washed clots as a source of clot-bound thrombin, providing fibrinogen and factor XIII to allow for clot extension, and tPA and plasminogen to allow for plasmin generation in situ and clot lysis. In FIG. 4A, absorbance at 340 nm was monitored in a plate reader every 30 seconds. Numbered turbidity profile curves in FIG. 4A contain reaction components identified as present (+) or lacking (−) in the table under the graph in FIG. 4B. In FIG. 4A, the result of a single experiment is shown, while in FIG. 4B the total area under the turbidity curve (AUC) is shown for six replicates (n=5±SD). In FIG. 4B, asterisks indicate statistically significant differences from condition 3, addition of 1.0 nM tPA without HSACHV3. Where present, the concentration of HSACHV3 is given above the bars, in slanted text; "cl. HSACHV3" corresponds to HSACHV3 completely activated by plasmin before addition to the reaction at 0.33 nM final concentration. Transfer of washed clots to a fresh source of fibrinogen allowed for continued clot growth in the absence of added thrombin or coagulation initiators (profile 1). In the absence of tPA, the maximum amount of HSACHV3 tested was without effect (33 nM). In the presence of tPA, the turbidity profile shifted from a plot that increased over time in a curvilinear fashion, to a parabolic formation and decay curve, but the total area under the curve was not altered. When increasing concentrations of tPA were titrated into the reaction, from 0.33 nM to 33 nM, the peak of the turbidity plot diminished in a dose-dependent manner, reaching statistical significance at the highest dose. Pre-activation of 0.33 nM HSACHV3 with plasmin under conditions shown to give full activation (FIG. 3) gave similar effects to the highest dose of HSACHV3 employed, with or without tPA (profiles 8 and 9), showing that liberated HV3 could largely eliminate clot formation in the system and that only a minor portion of the available HSACHV3 was being activated.

Figure 5A:
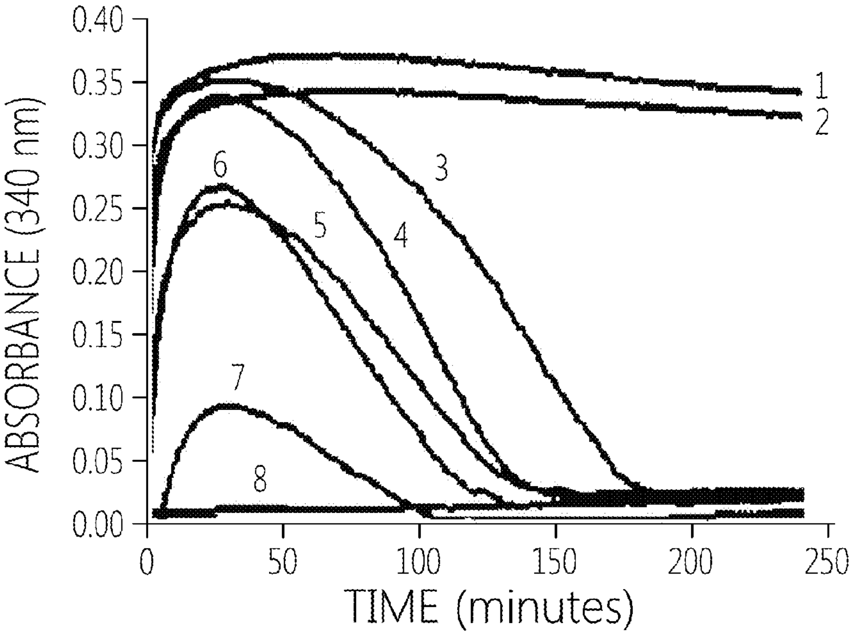
FIG. 5 illustrates the effects of HSACHV3 on clot formation and lysis in diluted plasma. (A) depicts the change in turbidity (absorbance at 340 nm) over time (in minutes) in normal human pooled citrated plasma diluted 2:3 (vol/vol), in Tris-buffered saline containing calcium chloride and 5 nM thrombin. (B) shows the area under the turbidity curve (AUC), in arbitrary units directly related to the product of absorbance and time, for a total of 7 experiments ±SD. * shows a statistically significant result.
Figure 5B:
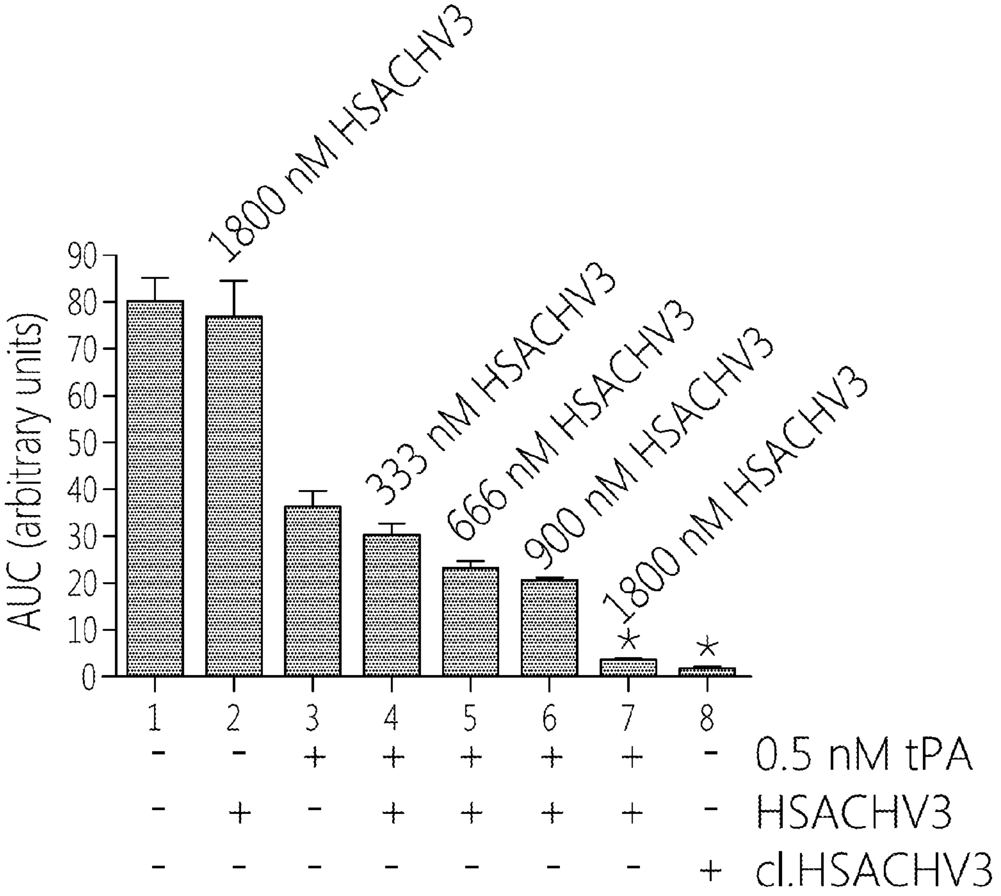

Before investigating HSACHV3 in vivo, a final series of experiments were performed in plasma, to obtain information additional to that gleaned in the clot-bound thrombin setting, that was likely most predictive of in vivo events. Citrated plasma was recalcified in the presence of 5 nM thrombin and 0.5 nM tPA, and the turbidity profiles and total AUC was followed in a similar fashion to that employed in the discontinuous clot-bound experiments. In FIG. 5A, where present, tPA was added to 0.5 nM. Absorbance at 340 nm was monitored in a plate reader every 30 seconds. Numbered turbidity profile curves in panel A contain reaction components identified as present (+) or lacking (−) in the table under the graph in FIG. 5B. As before, a single turbidity profile is presented in FIG. 5A, with quantification of it and four additional replicates shown in FIG. 5B (n=5±SD). In FIG. 5B, asterisks (black) indicate statistically significant differences from condition 3, addition of tPA without HSACHV3. Where present, the concentration of HSACHV3 is given above the bars, in slanted text; "cl. HSACHV3" corresponds to HSACHV3 completely activated by plasmin (which was neutralized by aprotinin before addition to the reaction) at 33 nM final concentration. In these experiments, plasma proteins approached physiological concentrations, and inhibitors of thrombin, plasmin, and tPA were present. Higher concentrations of HSACHV3 were therefore required to impact the more active processes taking place in this setting than in that shown in FIG. 4. Nevertheless, quantitatively similar patterns were observed. In the absence of tPA, stable clots rapidly formed (profile 1) which were unaffected by the presence of 1800 nM HSACHV3. Addition of 0.5 nM tPA into the system changed the profile to an asymmetrical parabolic curve corresponding to rapid clot formation and slower clot lysis (profile 3). Addition of increasing amounts of HSACHV3, from 333 nM to 1800 nM to the tPA-containing reaction reduced both peak height (FIG. 5A) and turbidity curve AUC in a dose-dependent manner, with the reduction associated with the highest HSACHV3 concentration becoming statistically significant. As before, much lower concentrations of HSACHV3, approximately 33 nM, were sufficient to abrogate clot formation, when quantitatively cleaved prior to addition to the system. The results suggest that not only does HSACHV3 inhibit clot-bound thrombin in a purified system, but that it demonstrates plasmin-dependent inhibition of coagulation that assists clot lysis, in a plasma clot system in vitro.

Clearance of Radiolabeled Proteins in Mice.

CD1 mice (average weight 25 g) were injected with radioiodinated proteins via the tail vein using a dose of $4.0\times10^6$ cpm radiolabeled protein in 0.1 mL of sterile saline and blood samples were collected at timed intervals by tail transections. A topical mixture of xylocalne and Clot-It™ (Evsco Pharmaceuticals, Buena, N.J.) was used to arrest bleeding between sample taking. Plasma was separated from blood cells by microcentrifugation (5 minutes at 13 000 g), and residual acid-precipitable plasma radioactivity was determined as previously described (Sheffield W P, et al., Br J Haematol 2004; 126: 565-573). In some experiments plasma samples were diluted and analyzed by SDS-PAGE and autoradiography. In vivo clearance experiments followed the terms of an Animal Utilization Protocol approved by the Animal Research Ethics Board of the McMaster University Faculty of Health Sciences.

Having demonstrated that HSACHV3 behaved as a plasmin-activatable thrombin inhibitor under a wide variety of experimental conditions in vitro, it was then sought to analyze its in vivo behavior. HV3, HSA, HSAHV3, and HSACHV3 were radioiodinated using the same conditions demonstrated not to interfere with cleavage of HSACHV3 by plasmin (FIG. 2C). The proteins were separately injected into groups of mice, and the residual protein-bound radioactivity in serially drawn plasma samples was followed over time following injection to construct clearance curves, as shown in FIG. 6A.

Figure 6A:
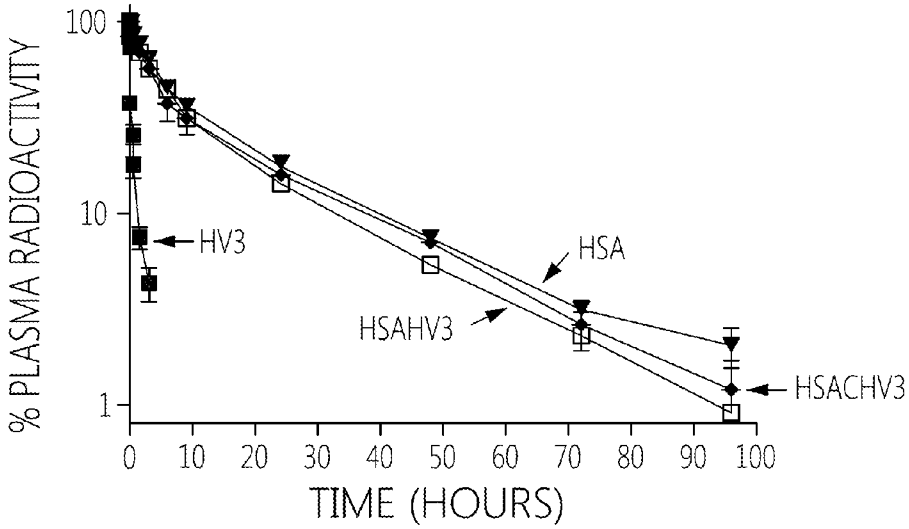
FIG. 6 illustrates the in vivo clearance of radioactive HV3 and HSA-related recombinant proteins in mice. (A) represents the percentage of residual plasma radioactivity normalized to the first, two minute post-injection sample, versus time in hours for HV3 (closed squares), HSA (closed inverted triangles), HSAHV3 (open squares), and HSACHV3 (closed diamonds). (B) is an autoradiogram of two dried 10% SDS-polyacrylamide gels containing plasma samples taken at times (in hours) post-injection, indicated in hours, from mice injected with $^{125}$I-HSA (left panel) or $^{125}$I-HSACHV3 (right panel). M refers to a molecular weight marker (in KDa).
Figure 6B:
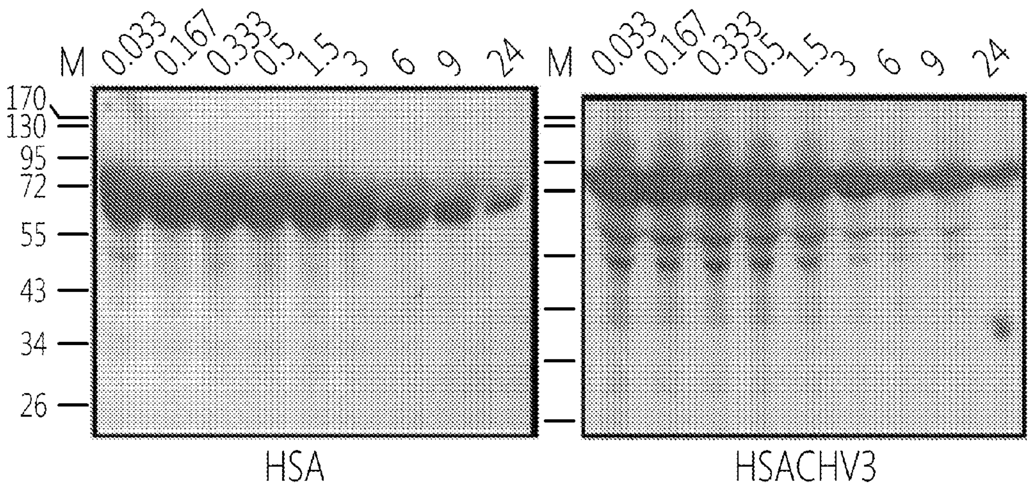

In FIG. 6A, data points represent the mean of 6-9 replicates ±SD. While the three recombinant HSA-containing proteins demonstrated highly similar clearance profiles, as evidenced by their largely overlapping curves, unfused HV3 was much more rapidly cleared. The clearance curve was essentially vertical, departing from being a line parallel to the y axis only after 90% of the dose had left the circulation. Hirudin clearance was not followed further, because the maximum amount of blood permitted to be drawn from the mice under the terms of our animal ethics approval, had been reached by this point. Detectable amounts of the HSA-containing proteins were still detectable in plasma 96 hours post-injection. To ensure that the protein-bound radioactivity that we were following did not correspond to polypeptide fragments, plasma samples were examined by electrophoresis and autoradiography. As shown in FIG. 6B, the great majority of both radiolabeled HSA and HSACHV3 was found to circulate in intact form; importantly, any minor, more rapidly migrating polypeptide species were present in the first plasma sample, suggesting that they did not derive from intravascular proteolysis.

Determination of the Effects of the Chimeras on Clotting Time.

CD1 mice were treated as described in the clearance experiments above, except that they were separately injected via the tail vein with 0.8 μmoles (1.5 mg) of HSA, HSAHV3, or HSACHV3 in 0.2 mL of sterile saline, or equimolar (0.18 mg) HV3, following the taking of a pre-injection blood sample using a heparinized capillary tube. Fifteen minutes later, tails were transected at a point 1 cm from the tip. Shed blood was collected on filter papers for 15 minutes, eluted in water, and quantified using $OD_{405}$ and $OD_{492}$ and a standard curve as previously described (Begbie M E, et al., Thromb Haemost 2005; 94: 1138-1147). At the close of the experiment a terminal blood sample was collected into sodium citrate by cardiac puncture. Plasma was separated from blood cells by microcentrifugation (5 minutes at 13,000 g). Prothrombin times (PT) were determined using 50 μl plasma combined with 100 μl pre-warmed Thromborel S (Dade Behring, Marburg, Germany), while activated partial thromboplastin times (aPTT) were determined by combining the same amount of mouse plasma with 50 μl aPTT reagent (Biomerieux, Durham, N.C.) and 50 μl 25 mM $CaCl_2$. In both cases clotting times were determined in a Labor Fibrintimer (Ahrensburg, Germany).

Figure 7A:
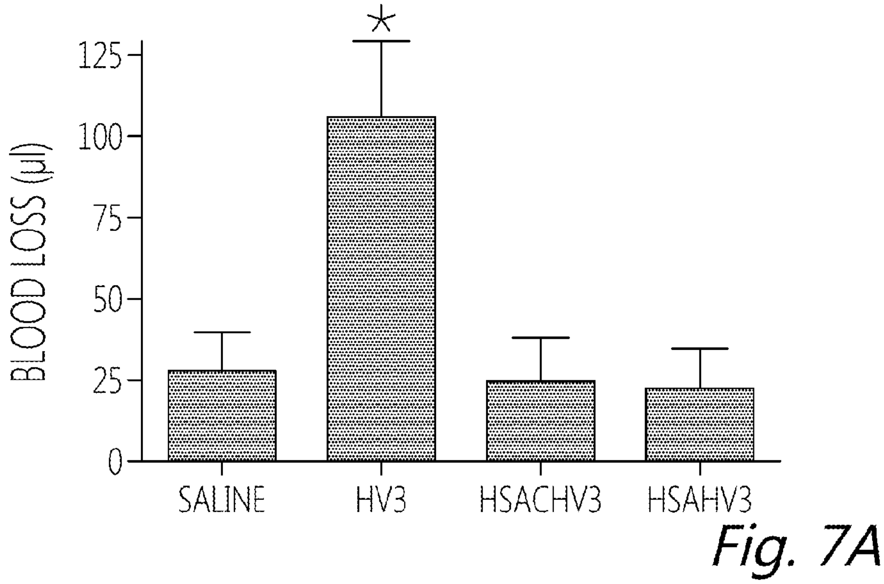
FIG. 7 illustrates the effects of recombinant equimolar (0.8 μmoles) doses protein of intravenous injection of HV3, HSA-CHV3, or HSAHV3 in saline, or saline in mice. (A) shows results on blood loss reported in μl from a standardized tail transection initiated 15 minutes after injection of saline or proteins to anaesthetized mice. (B) shows results on prothrombin time reported in seconds for plasma samples taken immediately before injection (PRE—white columns) and at the close of the 15 minutes shed blood collection phase of the experiment (POST—black columns). (C) shows results on activated partial thromboplastin times in seconds for plasma samples taken immediately before injection of proteins (PRE—white columns) or at the close of the 15 minutes shed blood collection phase of the experiment (POST—black columns).
Figure 7B:
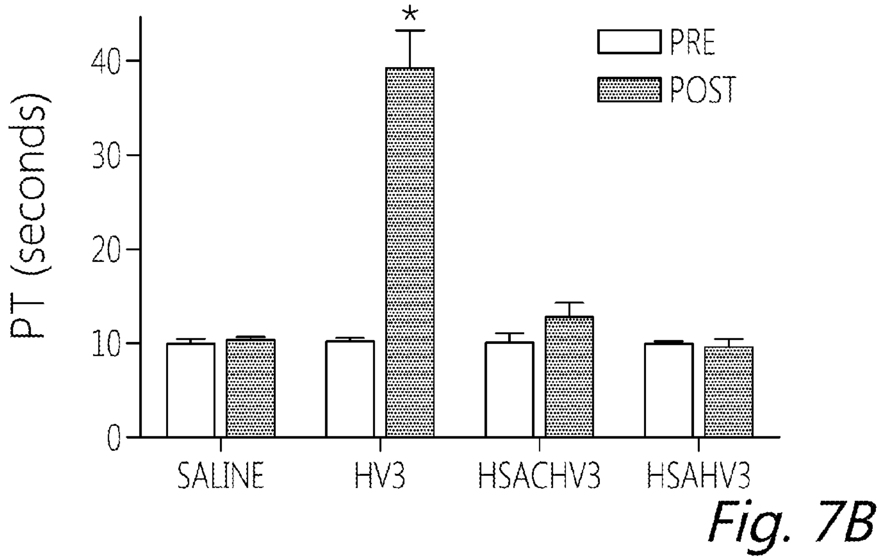
Figure 7C:
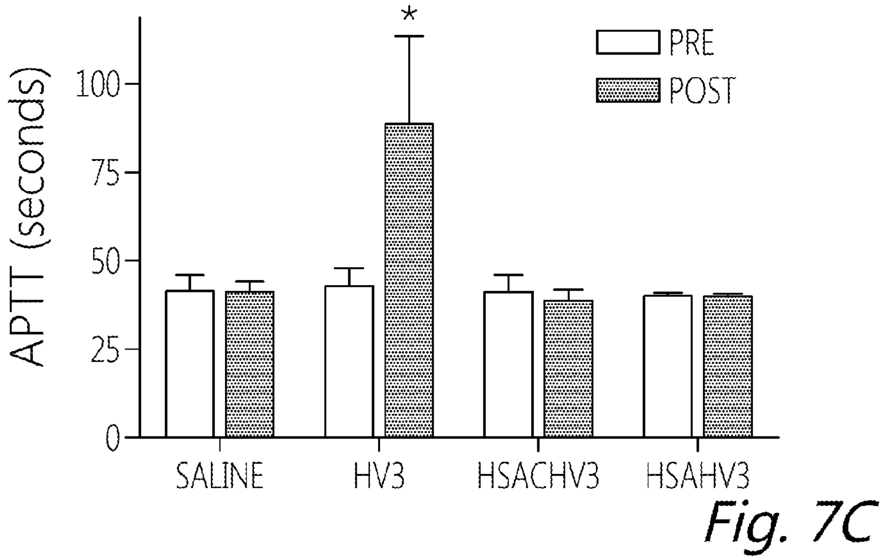

Equimolar 0.8 μmmole doses of HV3 (7.2 mg/kg body weight), HSAHV3 (60 mg/kg) and HSACHV3 (60 mg/kg) were injected into mice and blood loss was quantified in a tail transection model previously described by Begbie et al., (Thromb Haemost 2005; 94: 1138-1147). Mean blood loss did not differ in mice receiving saline, HSAHV3 or HSACHV3 (22 to 28 μl with SD of 12-14 μl), but was significantly increased, 4-fold, to 106±24 μl in mice receiving HV3 (FIG. 7A). This bleeding tendency was reflected in statistically significant elevations of a similar, 2- to 4-fold magnitude for both PT and APTT. As shown in FIGS. 7B and 7C, pretreatment and post-treatment coagulation times did not differ significantly, with the exception of the HV3-treated group. Taken together, these results indicate that the bleeding diathesis associated with HV3 injection has been avoided by rendering HV3 latent in chimeric, activatable HSACHV3. In FIG. 7A, shed blood was captured on filter paper for 15 minutes post-incision and quantified using spectrophotometry of eluted lysates. Data points are replicates of 6 determinations±SD. In FIGS. 7A to 7C, significant differences from saline controls are illustrated by an asterisk.

Ferric Chloride Mouse Model of Vena Cava Thrombosis.

Figure 8:
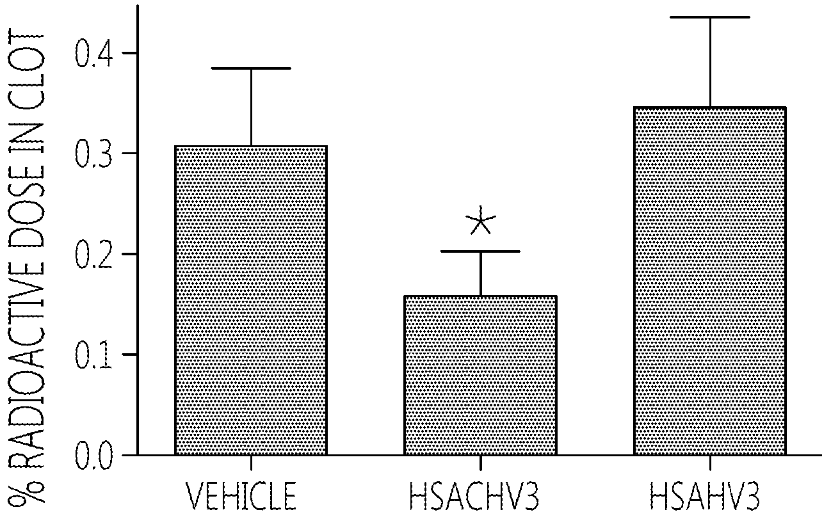
FIG. 8 illustrates the effects (percentage of radioactive dose in clot) of HSACHV3 or HSAHV3 in saline, or identical volumes of saline alone on the prevention of clot formation in vivo on a ferric mouse model. * shows a statistically significant result.

Anaesthetized CD1 mice with surgically exposed vena cava were co-injected with $1\times10^7$ cpm (approximately 2 μg) of human $^{125}$I-fibinogen and either saline (VEHICLE, n=6) or albumin fusion proteins HSACHV3 (n=6) or HSAHV3 (n=6) in a total volume of 0.2 ml, via the tail vein. Results are reported as the mean±standard deviation. The total dose of recombinant protein was 1.5 mg/mouse. Two minutes later, 2 mm×4 mm filter papers soaked with 10% (w/vol) solution of $FeCl_3$ were applied to the isolated vena cava for 3 minutes. This is a widely used experimental model for thrombosis in the mouse. Following filter paper removal, clots were allowed to age for 30 minutes before excision and determination of incorporated radioactivity by γ counting. The results are presented in FIG. 8 as the percentage of injected $^{125}$I-fibinogen found in the clot. The asterisk (*) indicates a statistically significant difference versus the VEHICLE control ($p<0.05$ by one-way ANOVA with Tukey-Cramer multiple comparisons post test using GraphPad InStat software). The results indicated that administration of activateable fusion protein HSACHV3 resulted in decreased fibrin deposition (smaller clots) in the model than no treatment, but that in contrast non-activatable fusion protein HSAHV3 had no effect. The bar graph values correspond to: VEHICLE, 0.31±0.08%; HSACHV3 0.16±0.04%; and HSAHV3 0.35±0.09%.

Statistical Methods.

Statistical analysis was performed using GraphPad InStat™ version 3.06 software (GraphPad Software, Inc, San Diego, Calif.) using parametric or non-parametric one-way analysis of variation (ANOVA) with Tukey-Kramer or Dunnett's multiple comparisons post-tests, depending on whether or not the data sets passed tests of normality and similarity of standard deviations.

EXAMPLE III

Construction and Characterization of AGP-Based Chimeras

Nucleic acid constructs. The human alpha-1 acid glycoprotein (AGP) cDNA was obtained by reverse transcription of RNA isolated from human hepatoma Hep G2 cells in culture, using oligonucleotides ML 13047 (5'-GAATGGATCC AAGGTGACTG CACCCTGC-3' (SEQ ID NO: 22)) and ML 13048 (5'-ATCGAATTCG GTACACATGT CGGGTTGG-3' (SEQ ID NO: 23)) using a Sensiscript™ reverse transcription kit (Qiagen, Chatsworth, Calif.). The reaction product was PCR-amplified using the same oligonucleotides and HotStarTaq™ heat-stable polymerase (Qiagen, Chatsworth, Calif.). The resulting PCR product was rendered blunt-ended by treatment with the Klenow fragment of *E. coli* DNA polymerase I and inserted into the SmaI site of plasmid pUC19. The resulting pUC19-AGP plasmid was PCR-amplified using oligonucleotides 07-1495 (5' ACGTCTCGAGA AAGACAGAT CCCATTGTGT GCCAACC-3'(SEQ ID NO: 24)) and 07-1494 (5'-CAGTGAATTCC CTAGTGATGG TGATGGGATT CCCCCTCCTC CTGTTT-3' (SEQ ID NO: 25)). The PCR product was digested with XhoI and EcoRI and inserted between the corresponding sites of plasmid pPICZ9ssamp to form plasmid pPICZ9ss-AGPH6. This plasmid served as a template for PCR using oligonucleotides AB11475 (5'-CCAACAGCAC AAATAACGGG-3' (SEQ ID NO: 26)) and ML 09-1808 (5' GATGGATCCG GATTCCCCCT CCTCCTGTTT CCT-3' (SEQ ID NO: 27)). The resulting PCR product was digested with XhoI and BamHI, the 651 by restriction fragment was combined with the 250 by BamHI/ApaI restriction fragment of pPICZ9ssHSACHV3H6 and the 4524 by XhoI-ApaI restriction fragment of pPICZ9ssamp in a three-part ligation. The resulting plasmid was designated pPICZ9ssAGPCHV3H6.

Figure 9:
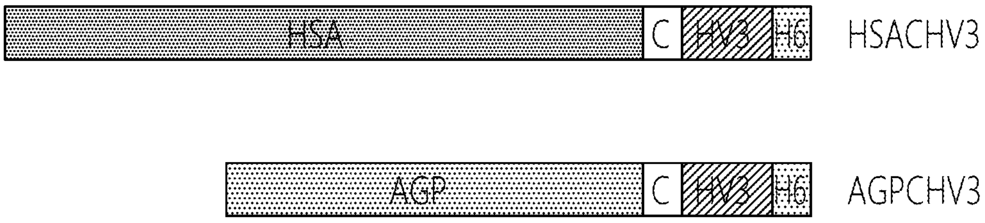
FIG. 9 Alpha-1 acid glycoprotein chimeric proteins. This figure illustrates a schematic diagram ($NH_2$ to COON) of a human serum albumin and hirudin variant 3 fusion protein with a plasmin cleavage site (HSACHV3 having the plasmin cleavage site of SEQ ID NO: 13) and an alpha-1 acid glycoprotein and hirudin variant 3 fusion protein with a plasmin cleavage site (AGPCHV3 having the plasmin cleavage site of SEQ ID NO: 13), in linear form.

FIG. 9 shows a schematic diagram comparing the HSACHV3 protein disclosed in Example II, and a further chimeric protein (AGPCHV3) using the acid-1-glycoprotein as a carrier. In FIG. 9, the protein components are shown in linear, N-terminal to C-terminal order. AGPCHV3 differs from HSACHV3 only in that the 584 amino acids of HSA have been replaced with the 183 amino acids of alpha-1 acid glycoprotein (AGP). HSA is not glycosylated, but AGP contains 5 sites of N-linked glycosylation. "C" denotes plasmin cleavage site, "HV3" the 66 amino acids of Hirudin Variant 3, and "H6" six histidine residues added to facilitate purification by nickel-chelate affinity chromatography. Both chimeric proteins were expressed in *Pichia pastoris*, yeast and purified from conditioned media, as described in Example II.

Figure 10:
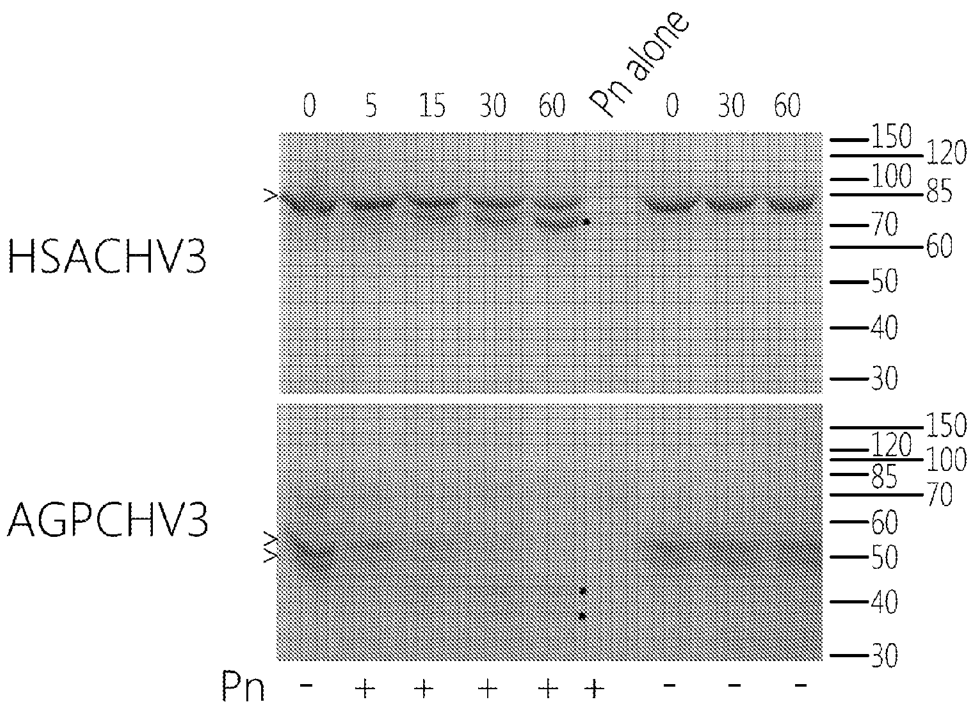
FIG. 10. Coomassie Blue-stained SDS acrylamide gels of the reaction between 1500 nM HSACHV3 and 600 nM plasmin (upper panel) and 4000 nM AGPCHV3 and 600 nM plasmin (lower panel). Numbers above the lanes denote time of reaction in minutes. Time zero lanes show purified HSA-CHV3 and AGPCHV3, respectively. Molecular weight markers are shown at right, in kilodaltons (kDa). Plasmin was faintly visible as a dimer in the 80-75 kDa range (see "Pn alone" lane). In the absence of plasmin, both fusion proteins were stable over the course of the experiment. The numbers on the right side of both gels refer to a molecular weight marker (in KDa).
Figure 11:
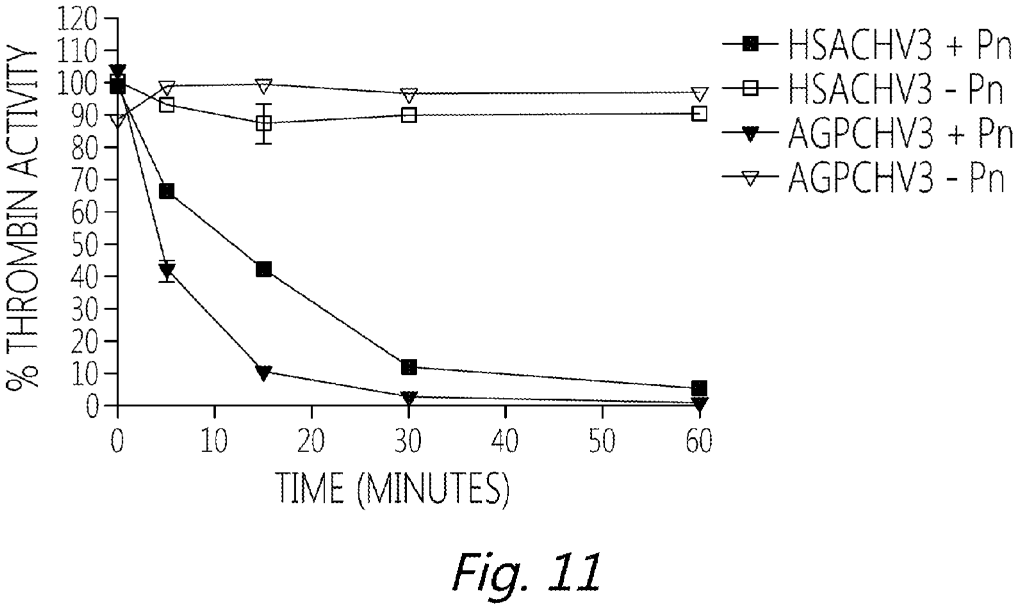
FIG. 11. presents the percentage of thrombin activity in function of time (minutes) for chimeric proteins HSACHV3 and AGPCHV3 (376 nM) incubated in the presence or absence of plasmin (600 nM). Closed square: HSACHV3 in the presence of plasmin; opened square: HSACHV3 in the absence of plasmin; closed triangle: AGPCHV3 in the presence of plasmin; opened triangle: AGPCHV3 in the absence of plasmin.

Chimeric proteins were purified and characterized on a SDS gel as described in Example II. FIG. 10 shows Coomassie Blue-stained SDS acrylamide gels of the reaction between 1500 nM HSACHV3 and 600 nM plasmin (upper panel) and 4000 nM HSACHV3 and 600 nM plasmin, respectively. Numbers above the lanes denote time of reaction in minutes. Time zero lanes show purified HSACHV3 and AGPCHV3, respectively. The latter protein does not stain as well as the former, likely due to its extensive glycosylation. It was also purified in multiple bands (see arrowheads in lower panel), suggesting N-terminal heterogeneity. The C-terminal HV3 and H6 domains are expected to be intact because of the affinity of AGPCHV3 protein for nickel-chelate resin. A time- and plasmin-dependent cleavage pattern of both proteins is shown, yielding a single product for HSACHV3 and two products for AGPCHV3 (highlighted by the black square in the upper panel and black squares in the lower). Liberated HV3 is too small to visualize on these gels, where molecular weight markers are shown at right, in kilodaltons. Plasmin was faintly visible as a dimer in the 80-75 kDa range (see "Pn alone" lane). In the absence of plasmin, both fusion proteins were stable over the course of the experiment.

Thrombin inhibitory activity of the various chimeras were assessed, as described in Example II. Supplementary FIG. 3, shown above, gives the quantitative results of experiments in which the fusion proteins (376 nM) were reacted with plasmin (600 nM) for varying times. The reaction products were then combined with thrombin and the rate of thrombin cleavage of a chromogenic substrate was determined using a plate reader. In the absence of plasmin, neither fusion protein had substantial effects upon the thrombin activity (see lines joining open symbols). In contrast, plasmin activated both AGPCHV3 and HSACHV3 to release thrombin inhibitory HV3. The results are shown as the mean of duplicate experiments, with error bars, where visible, indicating the range. While it appears that AGPCHV3 is more effective than HSACHV3 in inhibiting thrombin post-plasmin exposure, this is not possible to verify statistically without greater replication. A conservative interpretation of the data is that AGPCHV3 behaves similarly to HSACHV3 and is at least as effective a plasmin-activatable thrombin inhibitor. This interpretation is also supported by the results of similar experiments more closely resembling the conditions used in Supplementary FIG. 2, in which 1500 nM HSACHV3 or AGPCHV3 were combined with 600 nM plasmin prior to addition into a thrombin rate assay. The former reduced the rate of thrombin-mediated chromogenic substrate cleavage from 89.9% to 5.5%, and the latter from 78.2% to 4.9% of the control reaction rate (mean of 2 determinations).

Of course, the present invention is not to be limited to specific carrier protein or specific hirudin on the basis of the examples contained herein. One skilled in the art having in hand the present disclosure would know of other carriers or variants of hirudin to use, while still benefiting from the teaching of the present invention. For example, hirudin has a number of analogs or variants known in the art and all of them would be suitable for use in the present invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A chimeric hirudin protein comprising in this specific order:

- a carrier protein having a molecular weight equal to or greater than 40 kDa and being physiologically acceptable;
- a plasmin cleavage site covalently attached through its amino terminus to the carrier protein and consisting of the amino acid sequence of SEQ ID NO:7 or SEQ ID NO: 13;
- a scissile peptide bond covalently attached to the carboxyl terminus of said plasmin cleavage site; and
- a latent hirudin covalently and directly attached by its amino terminus to said scissile peptide bond on the carboxyl terminus of said plasmin cleavage site, wherein when cleaved at said scissile peptide bond in the presence of plasmin the latent hirudin is released from said chimeric hirudin protein as activated hirudin.

2. The chimeric hirudin protein of claim 1, wherein said carrier is a protein.

3. The chimeric hirudin protein of claim 2, wherein the protein is a plasma protein.

4. The chimeric hirudin protein of claim 3, wherein said plasma protein is albumin or alpha-1-acid glycoprotein.

5. The chimeric hirudin protein of claim, wherein said hirudin is a hirudin variant 3.

6. A method for limiting the growth of a clot in a subject in need thereof, said method comprising the step of administering to the subject the chimeric hirudin protein of claim 1 wherein said administration results in limiting the growth of said clot in the subject due to ability of said chimeric hirudin protein to reduce the size of the blood clot.

7. The method of claim 6, wherein the chimeric hirudin protein is administered with a thrombolytic agent.

8. The method of claim 6, wherein the chimeric hirudin protein is administered after the thrombolytic agent.

9. A method for reducing the size of a clot in a subject in need thereof, said method comprising the step of administering to the subject the chimeric hirudin protein of claim 1 wherein said administration results in reducing the size of said clot in the subject due to ability of said chimeric hirudin protein to reduce the size of the blood clot.

10. The method of claim 9, wherein the chimeric hirudin protein is administered with a thrombolytic agent.

11. The method of claim 9, wherein the chimeric hirudin protein is administered after a thrombolytic agent.

* * * * *

UNITED STATES PATENT AND TRADEMARK OFFICE

CERTIFICATE OF CORRECTION

PATENT NO. : 8,569,237 B2
APPLICATION NO. : 12/619919
DATED : October 29, 2013
INVENTOR(S) : William P. Sheffield It is certified that error appears in the above-identified patent and that said Letters Patent is hereby corrected as shown below:

In the Claims:

Claim 6, column 32, line 30, should read:

6. A method for limiting the growth of a blood clot in a subject in need thereof, said method comprising the step of administering to the subject the chimeric hirudin protein of claim 1 wherein said administration results in limiting the growth of said blood clot in the subject due to ability of said chimeric hirudin protein to limit the growth of the blood clot.

Claim 9, column 32, line 40, should read:

9. A method for reducing the size of a blood clot in a subject in need thereof, said method comprising the step of administering to the subject the chimeric hirudin protein of claim 1 wherein said administration results in reducing the size of said blood clot in the subject due to ability of said chimeric hirudin protein to reduce the size of the blood clot.

Signed and Sealed this
Twenty-eighth Day of January, 2014

Michelle K. Lee

Michelle K. Lee
*Deputy Director of the United States Patent and Trademark Office*

SEQUENCE LISTING

```
<160> NUMBER OF SEQ ID NOS: 27

<210> SEQ ID NO 1
<211> LENGTH: 27
<212> TYPE: DNA
<213> ORGANISM: Artificial Sequence
<220> FEATURE:
<223> OTHER INFORMATION: Oligonucleotide primer ML3205

<400> SEQUENCE: 1

ctggctggag tgcgatcttc ctgaggc                                    27


<210> SEQ ID NO 2
<211> LENGTH: 47
<212> TYPE: DNA
<213> ORGANISM: Artificial Sequence
<220> FEATURE:
<223> OTHER INFORMATION: Oligonucleotide primer ML3206

<400> SEQUENCE: 2

gccgctcgag tacgtaccat ggatcccaga tccgattttg gaggatg              47
```

<210> SEQ ID NO 3
<211> LENGTH: 35
<212> TYPE: DNA
<213> ORGANISM: Artificial Sequence
<220> FEATURE:
<223> OTHER INFORMATION: Oligonucleotide primer ML3207

<400> SEQUENCE: 3
gtattacgta cacagactgc acagagtctg gccag 35

<210> SEQ ID NO 4
<211> LENGTH: 32
<212> TYPE: DNA
<213> ORGANISM: Artificial Sequence
<220> FEATURE:
<223> OTHER INFORMATION: Oligonucleotide primer ML3208

<400> SEQUENCE: 4
atgcggccgc tactcatcat aggcatcctc ag 32

<210> SEQ ID NO 5
<211> LENGTH: 28
<212> TYPE: DNA
<213> ORGANISM: Artificial Sequence
<220> FEATURE:
<223> OTHER INFORMATION: Oligonucleotide primer ML3209

<400> SEQUENCE: 5
gatccggttc tgcaatgtct cgtattac 28

<210> SEQ ID NO 6
<211> LENGTH: 24
<212> TYPE: DNA
<213> ORGANISM: Artificial Sequence
<220> FEATURE:
<223> OTHER INFORMATION: Oligonucleotide primer ML3210

<400> SEQUENCE: 6
gtaatacgag acattgcaga accg 24

<210> SEQ ID NO 7
<211> LENGTH: 6
<212> TYPE: PRT
<213> ORGANISM: Artificial Sequence
<220> FEATURE:
<223> OTHER INFORMATION: CLE1 plasmin cleavage site

<400> SEQUENCE: 7

Gly Ser Ala Met Ser Arg
1 5

<210> SEQ ID NO 8
<211> LENGTH: 28
<212> TYPE: DNA
<213> ORGANISM: Artificial Sequence
<220> FEATURE:
<223> OTHER INFORMATION: Oligonucleotide primer ML3213

<400> SEQUENCE: 8
gatccaaaaa gtctcctgga cgtattac 28

<210> SEQ ID NO 9
<211> LENGTH: 24
<212> TYPE: DNA
<213> ORGANISM: Artificial Sequence
<220> FEATURE:

<223> OTHER INFORMATION: Oligonucleotide primer ML3214

<400> SEQUENCE: 9
gtaatacgtc caggagactt tttg 24

<210> SEQ ID NO 10
<211> LENGTH: 6
<212> TYPE: PRT
<213> ORGANISM: Artificial Sequence
<220> FEATURE:
<223> OTHER INFORMATION: CLE2 plasmin cleavage site

<400> SEQUENCE: 10

Lys Lys Ser Pro Gly Arg
1 5

<210> SEQ ID NO 11
<211> LENGTH: 28
<212> TYPE: DNA
<213> ORGANISM: Artificial Sequence
<220> FEATURE:
<223> OTHER INFORMATION: Oligonucleotide primer ML3211

<400> SEQUENCE: 11
gatccggctc tggaatctat cgtattac 28

<210> SEQ ID NO 12
<211> LENGTH: 24
<212> TYPE: DNA
<213> ORGANISM: Artificial Sequence
<220> FEATURE:
<223> OTHER INFORMATION: Oligonucleotide primer ML3212

<400> SEQUENCE: 12
gtaatacgat agattccaga gccg 24

<210> SEQ ID NO 13
<211> LENGTH: 6
<212> TYPE: PRT
<213> ORGANISM: Artificial Sequence
<220> FEATURE:
<223> OTHER INFORMATION: CLE3 plasmin cleavage site

<400> SEQUENCE: 13

Gly Ser Gly Ile Tyr Arg
1 5

<210> SEQ ID NO 14
<211> LENGTH: 61
<212> TYPE: DNA
<213> ORGANISM: Artificial Sequence
<220> FEATURE:
<223> OTHER INFORMATION: Oligonucleotide primer ML12007

<400> SEQUENCE: 14
catggaattc ttaatggtga cggtgatggt gtaagcctaa ggcagctcga cttgcagcaa 60
c 61

<210> SEQ ID NO 15
<211> LENGTH: 39
<212> TYPE: DNA
<213> ORGANISM: Artificial Sequence
<220> FEATURE:
<223> OTHER INFORMATION: Oligonucleotide primer ML12008

<400> SEQUENCE: 15

-continued gatcctcgag aaaagagacg cacacaagag tgaggttgc 39

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide primer ML12589

<400> SEQUENCE: 16
cagaggctca agtgtgccag 20

<210> SEQ ID NO 17
<211> LENGTH: 30
<212> TYPE: DNA
<213> ORGANISM: Artificial Sequence
<220> FEATURE:
<223> OTHER INFORMATION: Oligonucleotide primer ML12910

<400> SEQUENCE: 17
agctggatcc taaggcagct cgacttgcag 30

<210> SEQ ID NO 18
<211> LENGTH: 38
<212> TYPE: DNA
<213> ORGANISM: Artificial Sequence
<220> FEATURE:
<223> OTHER INFORMATION: Oligonucleotide for mobilizing HV3 codons in pGEXcle3HV3

<400> SEQUENCE: 18
agctttctcg agaaaagaat tacgtacaca gactgcac 38

<210> SEQ ID NO 19
<211> LENGTH: 55
<212> TYPE: DNA
<213> ORGANISM: Artificial Sequence
<220> FEATURE:
<223> OTHER INFORMATION: Oligonucleotide for mobilizing HV3 codons in pGEXcle3HV3

<400> SEQUENCE: 19
gcatggcggc cgccctagtg gtgatgatgg tggtgctcat cataggcatc ctcag 55

<210> SEQ ID NO 20
<211> LENGTH: 66
<212> TYPE: PRT
<213> ORGANISM: Hirudo sp.
<220> FEATURE:
<221> NAME/KEY: VARIANT
<222> LOCATION: (0)...(0)
<223> OTHER INFORMATION: Huridin variant 3

<400> SEQUENCE: 20

```
Ile Thr Tyr Thr Asp Cys Thr Glu Ser Gly Gln Asn Leu Cys Leu Cys
 1               5                  10                  15

Glu Gly Ser Asn Val Cys Gly Lys Gly Asn Lys Cys Ile Leu Gly Ser
            20                  25                  30

Gln Gly Lys Asp Asn Gln Cys Val Thr Gly Glu Gly Thr Pro Lys Pro
        35                  40                  45

Gln Ser His Asn Gln Gly Asp Phe Glu Pro Ile Pro Glu Asp Ala Tyr
    50                  55                  60

Asp Glu
65
```

<210> SEQ ID NO 21
<211> LENGTH: 6
<212> TYPE: PRT
<213> ORGANISM: Artificial Sequence
<220> FEATURE:
<223> OTHER INFORMATION: Concensus linker
<220> FEATURE:
<221> NAME/KEY: VARIANT
<222> LOCATION: (1)...(1)
<223> OTHER INFORMATION: Xaa = uncharged polar amino acid
<220> FEATURE:
<221> NAME/KEY: VARIANT
<222> LOCATION: (2)...(2)
<223> OTHER INFORMATION: Xaa = uncharged polar amino acid
<220> FEATURE:
<221> NAME/KEY: VARIANT
<222> LOCATION: (3)...(3)
<223> OTHER INFORMATION: Xaa = hydrophobic amino acid or an uncharged polar amino acid
<220> FEATURE:
<221> NAME/KEY: VARIANT
<222> LOCATION: (4)...(4)
<223> OTHER INFORMATION: Xaa = hydrophobic amino acid
<220> FEATURE:
<221> NAME/KEY: VARIANT
<222> LOCATION: (5)...(5)
<223> OTHER INFORMATION: Xaa = uncharged polar amino acid
<220> FEATURE:
<221> NAME/KEY: VARIANT
<222> LOCATION: (6)...(6)
<223> OTHER INFORMATION: Xaa = basic hydrophilic amino acid

<400> SEQUENCE: 21

Xaa Xaa Xaa Xaa Xaa Xaa
 1               5

<210> SEQ ID NO 22
<211> LENGTH: 28
<212> TYPE: DNA
<213> ORGANISM: Artificial Sequence
<220> FEATURE:
<223> OTHER INFORMATION: Oligonucleotide primer ML 13047

<400> SEQUENCE: 22
gaatggatcc aaggtgactg caccctgc 28

<210> SEQ ID NO 23
<211> LENGTH: 28
<212> TYPE: DNA
<213> ORGANISM: Artificial Sequence
<220> FEATURE:
<223> OTHER INFORMATION: Oligonucleotide primer ML 13048

<400> SEQUENCE: 23
atcgaattcg gtacacatgt cgggttgg 28

<210> SEQ ID NO 24
<211> LENGTH: 37
<212> TYPE: DNA
<213> ORGANISM: Artificial Sequence
<220> FEATURE:
<223> OTHER INFORMATION: Oligonucleotide primer 07-1495

<400> SEQUENCE: 24
acgtctcgag aaagacagat cccattgtgt gccaacc 37

<210> SEQ ID NO 25
<211> LENGTH: 47
<212> TYPE: DNA
<213> ORGANISM: Artificial Sequence
<220> FEATURE:
<223> OTHER INFORMATION: Oligonucleotide primer 07-1494

-continued

```
<400> SEQUENCE: 25

cagtgaattc cctagtgatg gtgatgggat tccccctcct cctgttt                   47


<210> SEQ ID NO 26
<211> LENGTH: 20
<212> TYPE: DNA
<213> ORGANISM: Artificial Sequence
<220> FEATURE:
<223> OTHER INFORMATION: Oligonucleotide primer AB11475

<400> SEQUENCE: 26

ccaacagcac aaataacggg                                                 20


<210> SEQ ID NO 27
<211> LENGTH: 33
<212> TYPE: DNA
<213> ORGANISM: Artificial Sequence
<220> FEATURE:
<223> OTHER INFORMATION: Oligonucleotide primer ML 09-1808

<400> SEQUENCE: 27

gatggatccg gattccccct cctcctgttt cct                                  33
```